(12) United States Patent
Kamei

(10) Patent No.: US 11,733,228 B2
(45) Date of Patent: Aug. 22, 2023

(54) GAS SAMPLE INTRODUCTION DEVICE, LEAK CHECK METHOD OF GAS SAMPLE INTRODUCTION DEVICE

(71) Applicant: SHIMADZU CORPORATION, Kyoto (JP)

(72) Inventor: Kota Kamei, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 21 days.

(21) Appl. No.: 17/525,221

(22) Filed: Nov. 12, 2021

(65) Prior Publication Data

US 2022/0170897 A1    Jun. 2, 2022

(30) Foreign Application Priority Data

Nov. 27, 2020    (JP) ................. 2020-196930

(51) Int. Cl.
  *G01N 33/00*    (2006.01)
  *G01N 1/22*    (2006.01)
(52) U.S. Cl.
  CPC ......... *G01N 33/007* (2013.01); *G01N 1/2226* (2013.01); *G01N 2001/2238* (2013.01)
(58) Field of Classification Search
  CPC ........ G01N 33/00; G01N 1/22; G01N 33/007; G01N 2001/2238; G01N 1/2226
  USPC ....................................................... 73/23.21
  See application file for complete search history.

(56) References Cited

U.S. PATENT DOCUMENTS

| | | | | |
|---|---|---|---|---|
| 8,074,492 B2 * | 12/2011 | Brockmann | ............ | G01M 3/22 73/1.05 |
| 10,281,445 B2 * | 5/2019 | Aono | .................... | G01M 3/205 |
| 2006/0099718 A1 * | 5/2006 | Tipler | ................. | G01N 1/2226 436/174 |
| 2006/0154371 A1 * | 7/2006 | Organiscak | ........... | G01M 3/226 436/3 |
| 2008/0016951 A1 * | 1/2008 | Lehmann | ............... | G01M 3/329 73/40 |
| 2010/0107730 A1 * | 5/2010 | Aono | ..................... | G01N 30/16 73/23.39 |
| 2014/0345365 A1 * | 11/2014 | Aono | .................... | G01M 3/205 73/40 |

(Continued)

FOREIGN PATENT DOCUMENTS

| | | |
|---|---|---|
| JP | 5146264 B2 | 12/2012 |
| JP | 5500027 B2 | 3/2014 |

(Continued)

*Primary Examiner* — Paul M. West
*Assistant Examiner* — Mark A Shabman
(74) *Attorney, Agent, or Firm* — Muir Patent Law, PLLC

(57) ABSTRACT

A gas sample introduction device includes a sample container connection flow path, a sample loop and a first flow path switching valve, having a first state in which the pressurizing gas is supplied to the sample container connection flow path via the sample loop and a second state in which the pressurizing gas is supplied to the sample container connection flow path without via the sample loop. A leak check method includes a first determination step of determining whether or not there is a gas leak by setting the first flow path switching valve to a first state and a second determination step of identifying a location of a gas leak by performing a second determination of whether or not there is a gas leak by setting the first flow path switching valve to a second state, when there is a gas leak in the first determination step.

8 Claims, 12 Drawing Sheets

(56) References Cited

U.S. PATENT DOCUMENTS

2015/0233874 A1\* 8/2015 Aono ................... G01N 30/24
                                            73/863.11
2016/0216172 A1\* 7/2016 Rella ....................... G01M 3/38

FOREIGN PATENT DOCUMENTS

| JP | 5768896 B2 | 7/2015 |
| JP | 5930049 B2 | 5/2016 |
| JP | 6127933 B2 | 4/2017 |

\* cited by examiner

GAS SAMPLE INTRODUCTION DEVICE, LEAK CHECK METHOD OF GAS SAMPLE INTRODUCTION DEVICE

CROSS-REFERENCE TO RELATED APPLICATIONS

This application claims priority to Japanese Patent Application No. 2020-196930 filed on Nov. 27, 2020 before the Japanese Patent Office, the contents of which are incorporated herein by reference in their entirety.

BACKGROUND OF THE INVENTION

Filed of the Invention

The present disclosure relates to a device for introducing a gas sample into a gas analysis device and a leak check method of the device.

Description of the Related Art

As a device for introducing a gas sample into a gas analysis device, a headspace sample introduction device is known. In a headspace sample introduction device, a liquid sample or a solid sample stored in a container is heated to a constant temperature to be volatilized, and this volatilized sample gas is collected from the upper space (headspace) in the container. This collected sample gas is introduced into a gas analysis device. A headspace sample introduction device is provided with gas pipes and therefore may cause a gas leak. Japanese Patent No. 5768896 discloses a headspace sample introduction device equipped with a gas leak determination means.

SUMMARY OF THE INVENTION

A conventional headspace sample introduction device has a gas leak determination means. However, the gas leak determination means can determine whether or not there is a gas leak but cannot identify the gas leak location. The present disclosure aims to provide a headspace sample analysis device capable of identifying a gas leak location.

Means for Solving the Problems

A gas sample introduction device according to the present disclosure is a device for introducing a sample gas into an analysis device.

A gas sample introduction device according to a first aspect of the present disclosure includes a sample container connection flow path, a pressurizing gas supply flow path, a gas discharge flow path, a sample loop, a first flow path switching valve, a first open/close valve, a second open/close valve, a pressure sensor, and a controller. The sample container connection flow path is connected to a space in a sample container. The pressurizing gas supply flow path is configured to supply a pressurizing gas for pressurizing an inside of the sample container. The gas discharge flow path is configured to discharge the pressurizing gas. The sample loop is configured to store the sample gas from the sample container. The first flow path switching valve is configured to switch between a first state and a second state. The first state is a state in which the sample loop is connected between the pressurizing gas supply flow path and the sample container connection flow path. The second state is a state in which the pressurizing gas supply flow path and the sample container connection flow path are connected without via the sample loop. The first open/close valve is arranged in a middle of the pressurizing gas supply flow path. The second open/close valve is arranged in a middle of the gas discharge flow path. The pressure sensor is configured to measure the pressure between the first open/close valve of the pressurizing gas supply flow path and the first flow path switching valve or between the second open/close valve of the gas discharge flow path and the first flow path switching valve. The controller is configured to control the first open/close valve, the second open/close valve, and the first flow path switching valve. The controller switches the first open/close valve from an open state to a closed state in a state in which the first flow path switching valve is in the first state and the second open/close valve is in a closed state and then performs a first determination of whether or not there is a gas leak, based on a measured value of the pressure sensor. When the controller has determined that there is a gas leak, the controller switches the first open/close valve from the open state to the closed state in a state in which the first flow path switching valve is in a second state and the second open/close valve is in a closed state and then performs a second determination of whether or not there is a gas leak, based on a measured value of the pressure sensor. With this, the controller identifies the location of the gas leak.

The gas sample introduction device according to a second aspect of the present disclosure further includes, in addition to the device according to the first aspect, a trap tube and a second flow path switching valve. The trap tube is configured to adsorb a predetermined component in the sample gas. The second flow path switching valve is capable of switching between a first state in which the trap tube is not connected to the sample loop and a second state in which the trap tube is connected to the sample loop. The controller performs the first determination in a state in which the second flow path switching valve is in the second state and then further performs the second determination of whether or not there is a gas leak in a state in which the second flow path switching valve has been switched to the first state. When the controller has determined that there is a gas leak in the second determination, the controller switches the first flow path switching valve from the second state to the first state. In this state, the controller switches the first open/close valve from the open state to the closed state and performs a third determination of whether or not there is a gas leak, based on a measured value of the pressure sensor. With this, the controller further identifies the location of the gas leak.

In a leak check method of a gas sample introduction device according to a third aspect of the present disclosure, the gas sample introduction device is provided with a sample container connection flow path, a pressurizing gas supply flow path, a gas discharge flow path, a sample loop, a first flow path switching valve, a first open/close valve, a second open/close valve, a pressure sensor, and a controller. The sample container connection flow path is connected to a space in a sample container. The pressurizing gas supply flow path supplies a pressurizing gas for pressurizing an inside of the sample container. The gas discharge flow path discharges the pressurizing gas. The sample loop is configured to store the sample gas from the sample container. The first flow path switching valve is configured to switch between a first state and a second state. The first state is a state in which the sample loop is connected between the pressurizing gas supply flow path and the sample container connection flow path. The second state is a state in which the pressurizing gas supply flow path and the sample container connection flow path are connected without via the sample loop. The first open/close valve is arranged in a middle of the pressurizing gas supply flow path. The second open/close valve is arranged in a middle of the gas discharge flow path. The pressure sensor is configured to measure a pressure between the first open/close valve of the pressurizing gas supply flow path and the first flow path switching valve or between the second open/close valve of the gas discharge flow path and the first flow path switching valve. The controller is configured to control the first open/close valve, the second open/close valve, and the first flow path switching valve. The leak check method according to the third aspect of the present disclosure includes a first determination step and a second determination step. The first determination step performs a determination of whether or not there is a gas leak such that the controller switches the first open/close valve from an open state to a closed state in a state in which the first flow path switching valve is in the first state and the second open/close valve is in a closed state and then performs the determination of whether or not there is a gas leak, based on a measured value of the pressure sensor. When the controller has determined that there is a gas leak in the first determination step, the controller performs the second determination step. In the second determination step, the controller switches the first open/close valve from an open state to a closed state in a state in which the first flow path switching valve is in a second state and the second open/close valve is in a closed state and then performs a second determination of whether or not there is a gas leak, based on a measured value of the pressure sensor. With this, the controller identifies the location of the gas leak.

The leak check method of a gas sample introduction device according to a fourth aspect of the present disclosure is a leak check method according to the third aspect of the present disclosure. The gas sample introduction device is further provided with a trap tube and a second flow path switching valve. The trap tube is configured to adsorb a predetermined component in the sample gas. The second flow path switching valve is capable of switching between a first state in which the trap tube is not connected to the sample loop and a second state in which the trap tube is connected to the sample loop. The leak check method according to the fourth aspect of the present disclosure further includes a third determination step. In the first determination step, the controller controls the second flow path switching valve so as to be switched to a second state in the first determination step. The controller further controls the second flow path switching valve so as to be switched to a first state in the second determination step. When the controller has determined that there is no gas leak in the second determination, the controller performs a third determination step. In the third determination step, the controller switches the first open/close valve from an open state to a closed state in a state in which the first flow path switching valve has been switched from the second state to the first state and performs a determination of whether or not there is a gas leak based on a measured value of the pressure sensor. With this, the controller further identifies the location of the gas leak.

The gas sample introduction device of the present disclosure can identify the leak location to some extent by switching the flow path to be pressurized and performing the leak check several times.

In particular, in the headspace gas analysis device described above, the user performs an operation for putting a lid on the sample container. Such an operation may cause a gas leak at the connection between the sample container connection flow path and the sample container. The sample loop is to be removed and installed in user maintenance. Therefore, the port of a flow path switching valve for connecting a sample loop may also cause a gas leak. When a gas leak has occurred, the gas sample introduction device of the present disclosure can determine whether or not a gas leak has occurred in a flow path including the sample container connection or whether or not a gas leak has occurred in a flow path including a sample loop.

EMBODIMENTS FOR CARRYING OUT THE INVENTION

Figure 1:
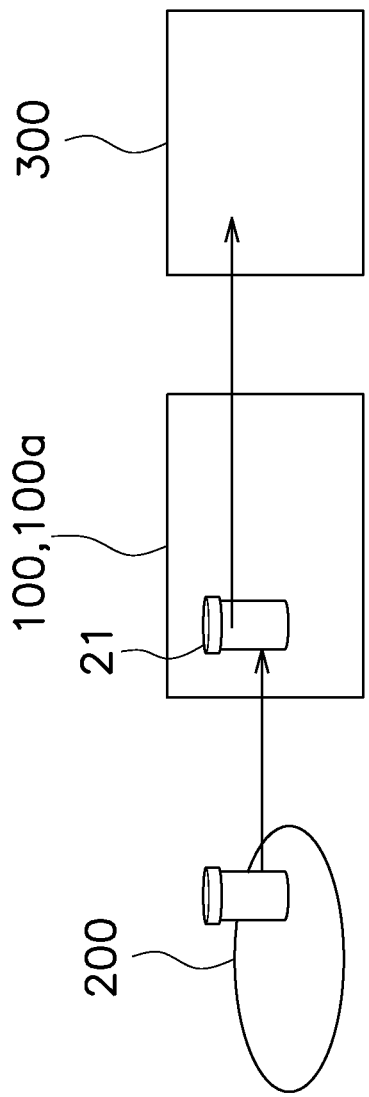
FIG. 1 is an entire schematic diagram of a device for performing a gas analysis by introducing a sample.

FIG. 1 shows an entire schematic view of a device for performing a gas analysis by introducing a liquid sample or a solid sample. The user puts a liquid sample or a solid sample in a sample container 21 and places this sample container 21 on a sample tray 200. The sample container 21 on the sample tray 200 is transferred by a transfer device to a predetermined position of a gas sample introduction device 100, 100a. The gas sample introduction device 100, 100a according to the present disclosure is a headspace sample introduction device. In the gas sample introduction device 100, 100a, the sample is vaporized into a sample gas. The sample gas is transferred to a gas analysis device 300 to be subjected to a gas analysis. The gas analysis device is, for example, a gas chromatograph. The gas chromatograph includes a separation column and a detector.

First Embodiment (1) Configuration of Gas Sample Introduction Device 100 (Loop Dedicated Device)

Figure 2:
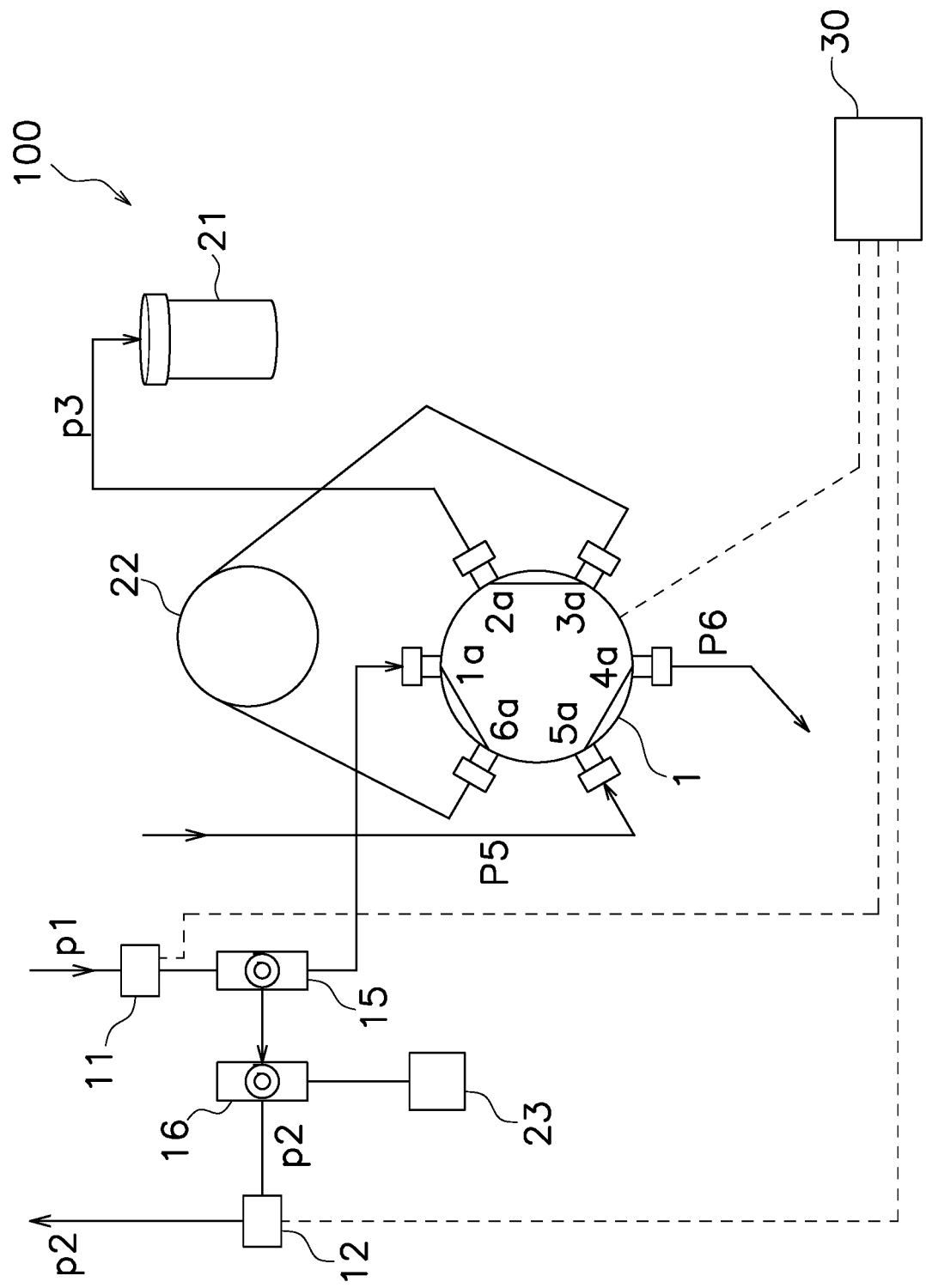
FIG. 2 is a diagram showing a configuration of a gas sample introduction device 100 (loop dedicated device) according to a first embodiment.

As shown in FIG. 2, a gas sample introduction device 100 of this embodiment is provided with a sample container connection flow path p3, a pressurizing gas supply flow path p1, a gas discharge flow path p2, a sample loop 22, a carrier gas supply flow path p5, an analysis device connection flow path p6, a first flow path switching valve 1, a first open/close valve 11, a second open/close valve 12, a pressure sensor 23, and a controller 30. The gas sample introduction device 100 includes a device for heating the sample container 21 and a device for piercing a needle into the sample container 21. The gas sample introduction device 100 may include a device for transferring the sample container 21 on the sample tray 200 to a predetermined position of the gas sample introduction device 100.

As will be described later, the gas sample introduction device 100a of a second embodiment includes both a sample loop 22 and a trap tube 24. In contrast, the gas sample introduction device 100 of the first embodiment does not include a trap tube 24. Therefore, the gas sample introduction device 100 of the first embodiment may be referred to as a loop dedicated device, and the gas sample introduction device 100a of the second embodiment may be referred to as a trap/loop dual-purpose device.

The sample container (vial) 21 includes a bottle made of glass and a lid (septum) made of silicone rubber or the like. In the sample container 21, a liquid sample or a solid sample is accommodated. A headspace is formed at the inner upper portion of the sample container 21. A user seals the inside of the sample container 21 by putting a lid on the bottle. A needle is pierced through the lid. As a result, the sample container connection flow path p3 and the headspace are communicated with each other. The gas sample introduction device 100 is further provided with a sample heating device (not shown). The sample heating device is controlled by the controller 30. The sample heating device heats the sample to a constant temperature for a certain time. By this heating, components of the sample with relatively lower boiling points are volatilized. The volatilized components are accumulated in the headspace.

As shown in FIG. 2, the sample container connection flow path p3 connects the headspace in the sample container 21 and the port 2a of the first flow path switching valve 1. A needle is arranged at the tip of the sample container connection flow path p3 on the sample container 21 side. By penetrating the needle through the lid of the sample container 21, the sample container connection flow path p3 can be connected to the headspace in the sample container 21.

The pressurizing gas supply flow path p1 is a flow path for supplying a pressurizing gas for pressurizing the inside of the sample container 21. The pressurizing gas is, for example, an inert gas, such as, e.g., helium, nitrogen, and the like. The pressurizing gas is controlled to a predetermined gas pressure higher than the atmospheric pressure. In the pressurizing gas supply flow path p1, one end thereof is connected to a constant pressure gas source and the other end thereof is connected to the port 1a of the first flow path switching valve 1. The constant pressure gas source is, for example, a pressure controller. In the pressurizing gas supply flow path p1, as shown in FIG. 2, from the constant pressure gas source side, a first open/close valve 11, and a branch pipe 15 are connected in this order. By opening the first open/close valve 11, the high pressure of the pressurizing gas is supplied to the port 1a of the first flow path switching valve 1.

In the gas discharge flow path p2, one end thereof is connected to a constant pressure gas source, and the other end thereof is connected to the branch pipe 15 on the pressurizing gas supply flow path p1. The constant pressure gas source is, for example, a pressure controller. The gas pressure of the gas discharge flow path p2 is higher than the atmospheric pressure and lower than the pressure of the pressurizing gas. The gas pressure of the gas discharge flow path p2 may be produced by depressurizing the gas pressure of the pressurizing gas. In the gas discharge flow path p2, from the branch pipe 15 toward the constant pressure source, a branch pipe 16 and a second open/close valve 12 are connected in this order. To the branch pipe 16, a pressure sensor 23 is connected.

By closing the second open/close valve 12, the pressure on the pressurizing gas supply flow path p1 side is maintained.

The first open/close valve 11 and the second open/close valve 12 each may be a solenoid valve.

The pressure sensor 23 measures the gas pressure of the branch pipe 16. By closing the second open/close valve 12, the pressure sensor 23 can measure the pressure of the pressurizing gas supply flow path p1 side. In this embodiment, the pressure sensor 23 (and the branch pipe 16) is arranged between the second open/close valve 12 of the gas discharge flow path p2 and the branch pipe 15. However, the pressure sensor 23 (and the branch pipe 16) may be arranged between the first open/close valve 11 of the pressurizing gas supply flow path p1 and the port 1a of the first flow path switching valve 1. The pressure sensor 23 can measure the pressure between the first open/close valve 11 in the pressurizing gas supply flow path p1 and the port 1a of the first flow path switching valve 1.

The sample loop 22 is also referred to as a measuring tube. The sample loop 22 has a predetermined volume and can accommodate the sample gas. The sample loop 22 is connected to the port 6a of the first flow path switching valve 1 and the port 3a thereof.

The carrier gas introduces the sample gas to the analysis device 300. The carrier gas is, for example, an inert gas, such as, e.g., helium and nitrogen, or hydrogen. The carrier gas may be the same as or different from the pressurizing gas, but hydrogen is not used as the pressurizing gas. The carrier gas supply flow path p5 connects the carrier gas supply source and the port 5a of the first flow path switching valve 1.

The analysis device connection flow path p6 connects the analysis device 300 and the port 4a of the first flow path switching valve 1.

The first flow path switching valve 1 has six ports 1a to 6a. The first flow path switching valve 1 switches the port connection status between a first state and a second state. In the first state, as shown in FIG. 2, the first flow path switching valve 1 connects the port 6a and the port 1a, connects the port 2a and the port 3a, and connects the port 4a and the port 5a. The first state is also referred to as a load state. In the second state, the first flow path switching valve 1 connects the port 1a and the port 2a, connects the port 3a and the port 4a, and connects the port 5a and the port 6a. The second state is also referred to as an inject state.

Note that a formation showing the open/close state of the first open/close valve 11 and the second open/close valve 12 and a formation indicating whether the first flow path switching valve 1 is in the first state or in the second state are referred to as valve formations. The valve formations mainly at the time of a leak check are shown in Table 1 as valve formations A1 to A4. When using the same valve formation at the time of introducing a sample, the valve formations A1 to A4 are used as appropriate.

TABLE 1

| Valve formation | First open/close valve 11 | Second open/close valve 12 | First flow path switching valve 1 |
|---|---|---|---|
| A1 | Open | Close | First state (load) |
| A2 | Close | Close | First state (load) |
| A3 | Open | Close | Second state (inject) |
| A4 | Close | Close | Second state (inject) |

The controller 30 is a computer. The controller 30 includes a processor and a memory. The controller 30 may further include a display and a user input means, such as, e.g., a keyboard, a mouse, and a touch panel. Programs are stored in the memory. The programs may be a sample introduction program, a leak check program, or the like. The processor executes the programs. The controller 30 controls the first open/close valve 11, the second open/close valve 12, the first flow path switching valve 1, and the sample heating device (not shown). The controller 30 may further control a device for transferring the sample from the sample tray to the gas sample introduction device 100 and a device for piercing the needle into the sample container 21.

(2) Method of Introducing Gaseous Sample into Analysis Device by Gas Sample Introduction Device 100

Next, a method for introducing the gaseous sample into the analysis device by the gas sample introduction device 100 will be described.

The user inserts a liquid sample or a solid sample into the bottle of the sample container 21 and closes the bottle with a lid in a sealed manner. Then, the user places the sample container 21 on the sample tray 200. The sample container 21 is transferred from the sample tray 200 to a predetermined position of the gas sample introduction device 100.

The controller 30 heats the sample container 21 by a heating device at a constant temperature for a predetermined time. Gas components are generated from the liquid sample or the solid sample, and the generated gas components are accumulated in the headspace in the sample container 21. By piercing the needle connected to the sample container connection flow path p3 into the lid of the sample container 21, the sample container connection flow path p3 and the headspace in the sample container 21 are communicated with each other.

In a state in which the first flow path switching valve 1 is set to the first state (load state) and the second open/close valve 12 is closed, the first open/close valve 11 is changed from the closed state to the open state (valve formation A1). The pressure of the pressurizing gas is supplied from the pressurizing gas supply flow path p1 to the headspace in the sample container 21 via the sample loop 22 and the sample container connection flow path p3 (see FIG. 5). In other words, the headspace becomes the pressure of the pressurizing gas.

Next, in a state in which the first flow path switching valve 1 is held in the first state (load state), the first open/close valve 11 is closed, and the second open/close valve 12 is opened. This in turn causes the pressurizing gas and the sample gas to flow from the headspace, through the sample container connection flow path p3, the sample loop 22, and the gas discharge flow path p2, in a direction toward the outside of the device 100. Here, the gas discharge flow path p2 is controlled to a constant pressure higher than the atmospheric pressure, so when the pressure has reached a constant pressure, the gas flow stops. In this operation, the sample gas is accommodated in the sample loop 22.

Next, the first flow path switching valve 1 is switched to the second state (inject state), and the carrier gas is supplied to the carrier gas supply flow path p5. The carrier gas flows through the analysis device connection flow path p6 together with the sample gas accommodated in the sample loop 22 and is supplied to the analysis device 300 (see FIG. 6).

(3) Leak Check Method of Gas Sample Introduction Device 100

Figure 3:
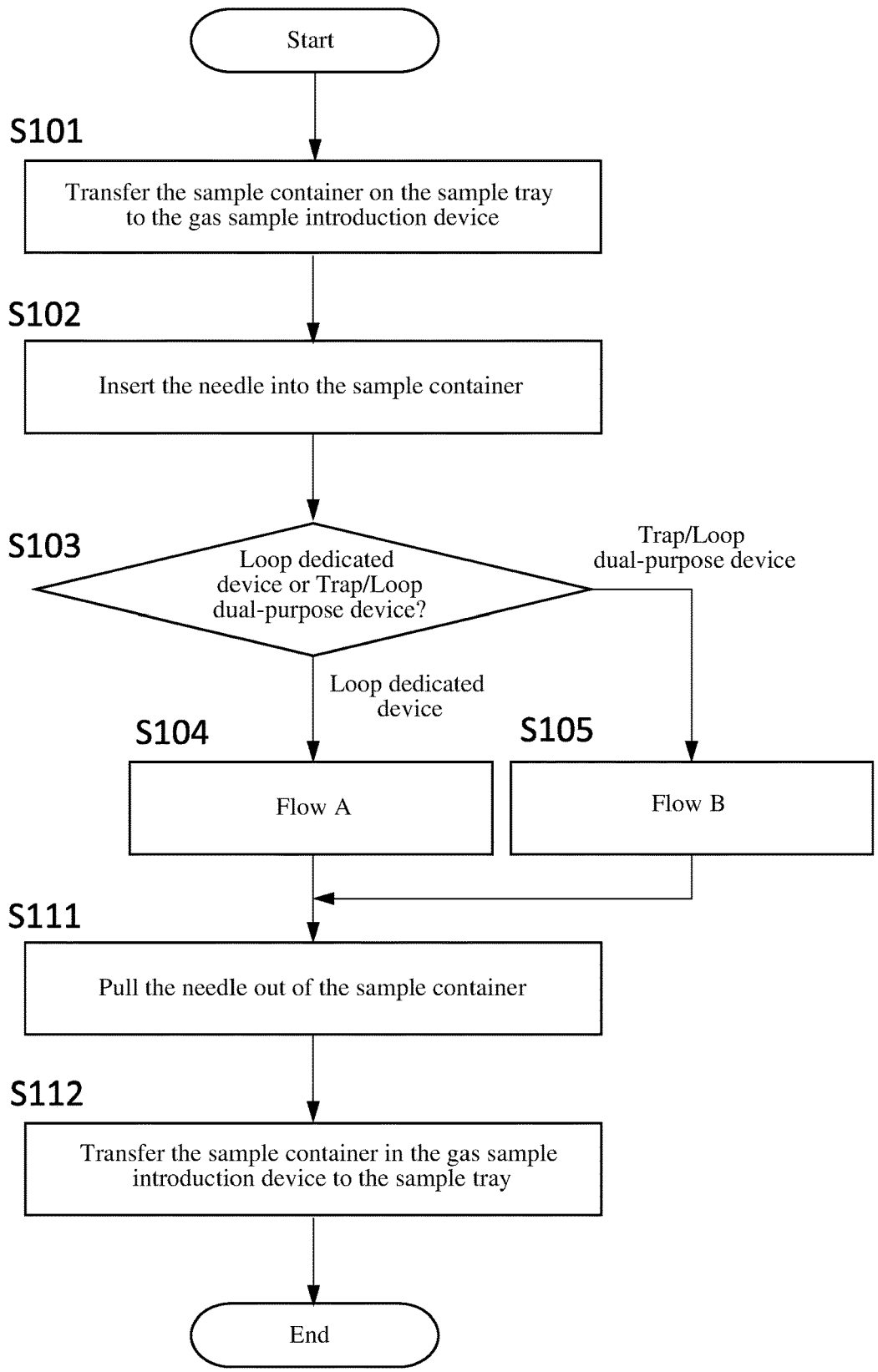
FIG. 3 is a flowchart showing a part of a leak check method using the gas sample introduction device 100, 100a according to the first and second embodiments.
Figure 4:
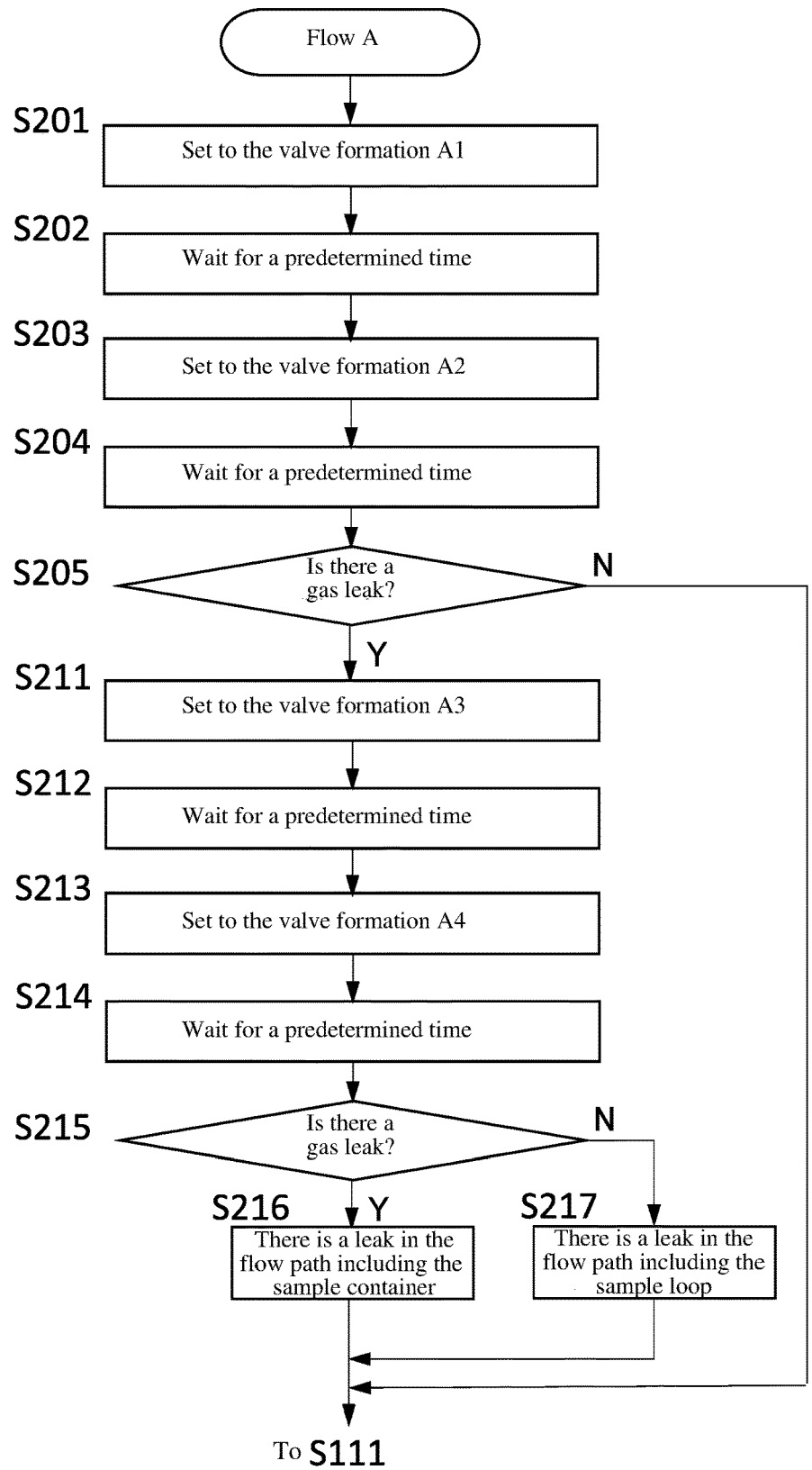
FIG. 4 is a flowchart showing a part of the leak check method of the gas sample introduction device 100 according to the first embodiment.

Next, a leak check method of the gas sample introduction device 100 will be described with reference to the attached figures. FIG. 3 and FIG. 4 are flowcharts showing the leak check method.

As a preparation, the user puts a lid on the bottle of the sample container 21 to seal the inside and places this bottle on the sample tray. A sample or a dummy sample may be sealed in the sample container, or no sample may be sealed therein.

In a state of being prepared as described above, the user instructs the controller 30 to perform a leak check. For example, the user inputs an instruction by means of a computer input means. With this, the leak check program stored in the memory of the controller 30 is executed.

First, in Step S101, the transfer device transfers the sample container 21 on the sample tray 200 to a predetermined position of the gas sample introduction device 100.

Next, in Step S102, the gas sample introduction device 100 inserts a needle into the inside of the sample container 21. As a result, the headspace in the sample container 21 and the sample container connection flow path p3 are connected to each other. In introducing the gas sample, the sample container 21 is heated, but at the time of performing the leak check, the sample container 21 may or may not be heated.

Next, in Step S103, the controller 30 determines whether the gas sample introduction device is a loop dedicated device or a trap/loop dual-purpose device. In this embodiment, since it is a loop dedicated device, the flow proceeds to the flow A (see FIG. 4).

The flow A shown in FIG. 4 is the main processing of the leak check. The flow A includes a first determination step (S201 to S205) and a second determination step (S211 to S217). The first determination step (S201 to S205) determines whether or not there is a gas leak in the main flow path of the gas sample introduction device 100. The second determination Step (S211 to S217) identifies the position of the gas leak.

The first determination step is as follows.

Figure 5:
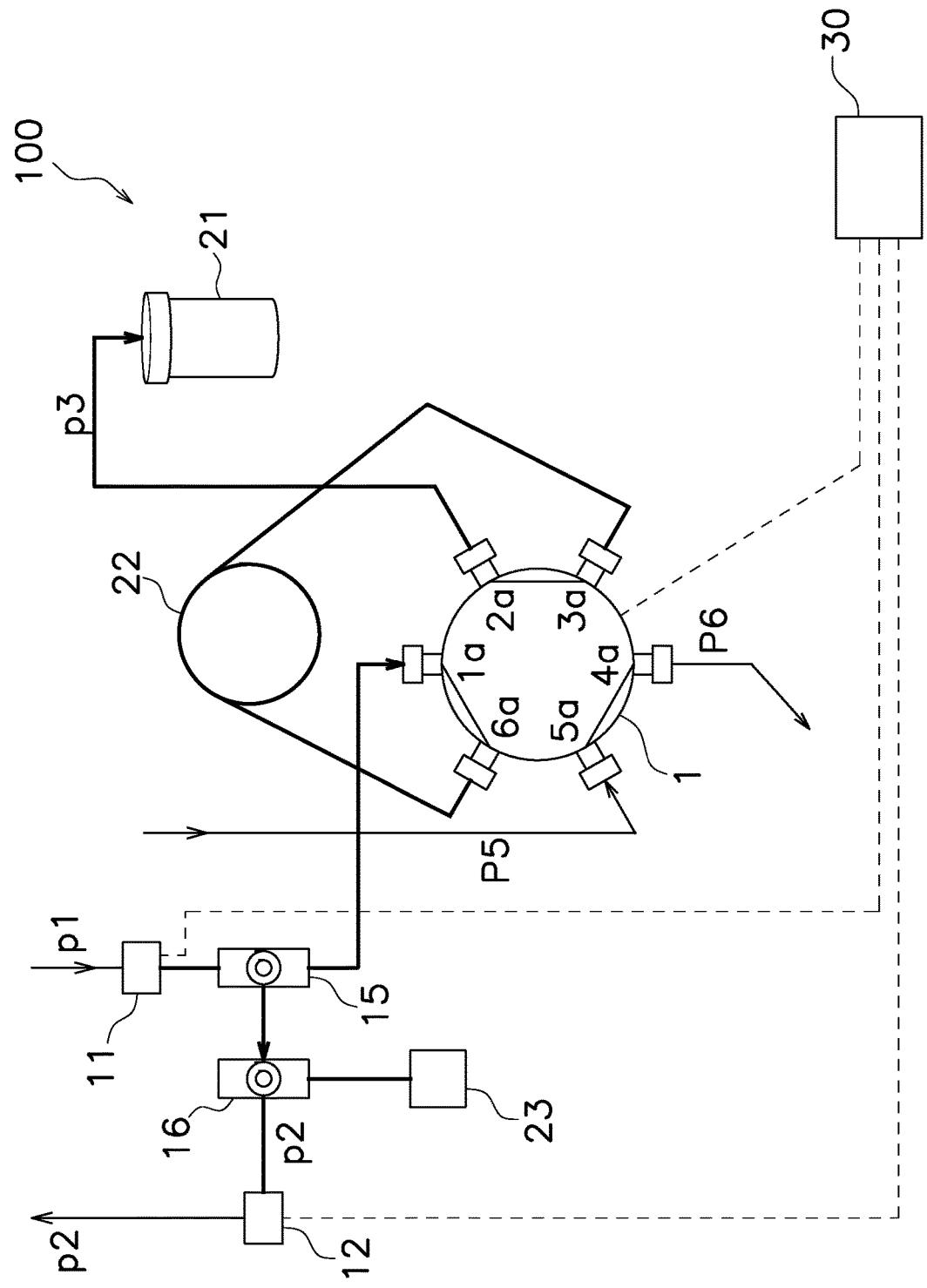
FIG. 5 is a diagram showing a thick line portion that becomes a high pressure in the first determination step during the leak check of the gas sample introduction device 100 of the first embodiment.

First, in Step S201, the controller 30 sets the valve formation to the valve formation A1. More specifically, the controller 30 sets the second open/close valve 12 to a closed state and the first flow path switching valve 1 to the first state (load state). In this state, the controller 30 changes the first open/close valve 11 from the closed state to the open state. With this, the portion of the gas sample introduction device 100 indicated by the thick line in FIG. 5 is pressurized with the pressurizing gas. Then, the elapse of a preset predetermined time is waited (S202). The predetermined time means a time from when there is no gas leak, the pressurizing gas flows from the pressurizing gas supply flow path p1 to the entire flow paths shown by the thick line until when the pressure measured by the pressure sensor 23 is stabilized.

Next, in Step S203, the controller 30 sets the valve formation to the valve formation A2. Specifically, without changing the states of the second open/close valve 12 and the first flow path switching valve 1, the controller 30 changes the first open/close valve 11 from the open state to the closed state. With this, the portion of the gas sample introduction device 100 indicated by the thick line in FIG. 5 is sealed in a state of being pressurized with the pressurizing gas. That is, the sealed portions are the portion of the pressurizing gas supply flow path p1 on the side of the first flow path switching valve 1 than the first open/close valve 11, the portion of the gas discharge flow path p2 between the second open/close valve 12 and the branch pipe 15, the ports 1a, 6a, 3a, and 2a of the first flow path switching valve 1, the sample loop 22, the sample container connection flow path p3, and the inside of the sample container 21. Then, the elapse of a preset predetermined time is waited (S204). The predetermined time here may be the same as or different from the predetermined time in Step S202

Next, in Step S205, the controller 30 determines whether or not a gas leak has occurred. More particularly, the controller 30 determines whether or not the measured value of the pressure sensor 23 is a normal (no gas leak) gas pressure. Normally, when the measured pressure is close to the pressure of the pressurizing gas or sufficiently high, the controller 30 determines that it is normal (no gas leak). On the other hand, when the measured pressure is considerably lower than the pressure of the pressurizing gas, the controller 30 determines that it is not normal (there is a gas leak). When it is determined that there is no gas leak, it returns to FIG. 3, and the process proceeds to Step S111. When it is determined that there is a gas leak, the process proceeds to Step S211 of the second determination step.

Next, the second determination step will be described.

Figure 6:
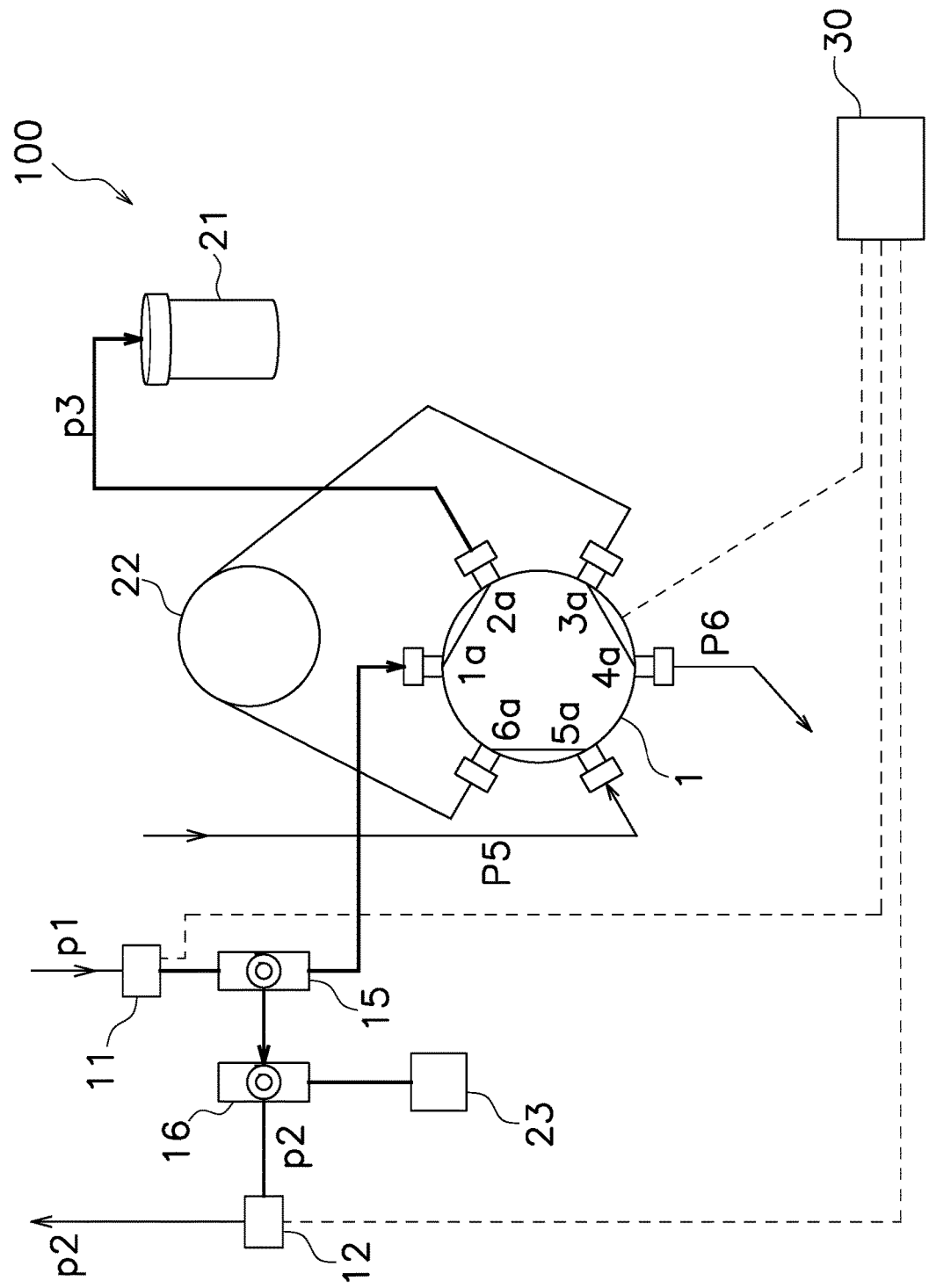
FIG. 6 is a diagram showing a thick line portion that becomes a high pressure in the second determination step during the leak check of the gas sample introduction device 100 of the first embodiment.

In Step S211, the controller 30 sets the valve formation to the valve formation A3. More specifically, in a state in which the second open/close valve 12 is in a closed state and the first flow path switching valve 1 is in the second state (inject state), the controller 30 changes the first open/close valve 11 from the closed state to the open state. With this, the portion of the gas sample introduction device 100 indicated by the thick line in FIG. 6 is pressurized with the pressurizing gas. Then, the elapse of a preset predetermined time is waited (S212). The predetermined time means a time from when the pressurizing gas flows through the pressurizing gas supply flow path p1 until when the pressure measured with the pressure sensor 23 is stabilized, in a case where there is no gas leak. The predetermined time in Step S212 may be the same as or different from the predetermined time in Step S202.

Next, in Step S213, the controller 30 sets the valve formation to the valve formation A4. Specifically, the controller 30 changes the first open/close valve 11 from the open state to the closed state without changing the states of the second open/close valve 12 and the first flow path switching valve 1. With this, the portion of the gas sample introduction device 100 indicated by the thick line in FIG. 6 is sealed in a state of being pressurized with the pressurizing gas. That is, the sealed portions are the portion of the pressurizing gas supply flow path p1 on the side of the first flow path switching valve 1 than the first open/close valve 11, the portion of the gas discharge flow path p2 between the second open/close valve 12 and the branch pipe 15, the ports 1a and 2a of the first flow path switching valve 1, the sample container connection flow path p3, and the inside of the sample container 21. Then, the elapse of a preset predetermined time is waited (S214). The predetermined time here may be the same as or different from the predetermined time in Step S212. Next, in Step S215, the controller 30 determines whether or not there is a gas leak. More particularly, the controller 30 determines whether the measured value of the pressure sensor 23 is a normal (no gas leak) gas pressure. Normally, when the measured pressure is sufficiently high close to the pressure of the pressurizing gas, the controller determines that it is normal (there is no gas leak). On the other hand, when the measured pressure is considerably lower than the pressure of the pressurizing gas, the controller determines that it is not normal (there is a gas leak).

When the controller 30 determines that there is a gas leak in Step S215, the controller determines that there is a gas leak in the portion pressurized in the second determination step and the portion indicated by the thick line in FIG. 6 (S216). The controller 30 determines that there is a gas leak at one of the portion of the pressurizing gas supply flow path p1 on a side of the first flow path switching valve 1 than the first open/close valve 11, the portion of the gas discharge flow path p2 between the second open/close valve 12 and the branch pipe 15, the ports 1a and 2a of the first flow path switching valve 1, the sample container connection flow path p3, and the inside of the sample container 21. That is, the controller 30 determines that there is a gas leak at the flow path including the sample container connection flow path p3.

When it is determined that there is no gas leak in Step S215, it is determined that there is a gas leak at the portion pressurized in the first determination step and not pressurized in the second determination step. That is, it is determined that there is a gas leak in the sample loop 22 or at the port 6a or 3a of the first flow path switching valve 1.

Returning to FIG. 3, the controller 30 controls such that the needle is pulled out of the sample container 21 (S111) and the sample container 21 is transferred to the sample tray 200 (S112), and ends the processing.

In the gas sample introduction device 100 and the sample container 21 of this embodiment, the portions which are considered that a gas leak particularly occurs are the sample container 21 in which the user puts a lid and the ports 6a and 3a of the first flow path switching valve 1 to which the sample loop 22 is connected. According to the leak check method of the present disclosure, it is possible to specify in which flow path a gas leak has occurred by the gas leak determination in Step S215.

Note that in the leak check method (program) of this embodiment, in Step S103, it is determined whether it is for a loop dedicated device or a trap/loop dual-purpose device. When it is for a method (program) used exclusively for a loop dedicated device, the flow may proceed to the flow A by skipping Step S103.

Further, in the leak check method of this embodiment, even in the first determination step or in the second determination step, it is determined whether there is a gas leak by introducing the pressuring gas, sealing the pressurized gas flow path, and checking the degree of decrease in the gas pressure. In either one of or both determination steps, it may be configured such that it is determined whether or not there is a gas leak in a flow path by checking the degree of increase in the pressure in a gas flow in the process of introducing the pressurizing gas by changing the state of the first open/close valve from the closed state to the open state.

Note that the gas sample introduction device 100 of this embodiment has the flow path configuration shown in FIG. 2, but the present disclosure is not limited thereto. For example, in the present disclosure, the first flow path switching valve 1 with six ports is used, but a first flow path switching valve 1 with a different number of ports may be used. Further, the valve formation is not necessarily the same as that of this embodiment. As long as the flow path capable of being pressurized by a pressurizing gas can be switched by switching the valve formations, some gas leak locations can be identified.

Second Embodiment (4) Configuration of Gas Sample Introduction Device 100a (Trap/Loop Dual-Purpose Device)

Figure 7:
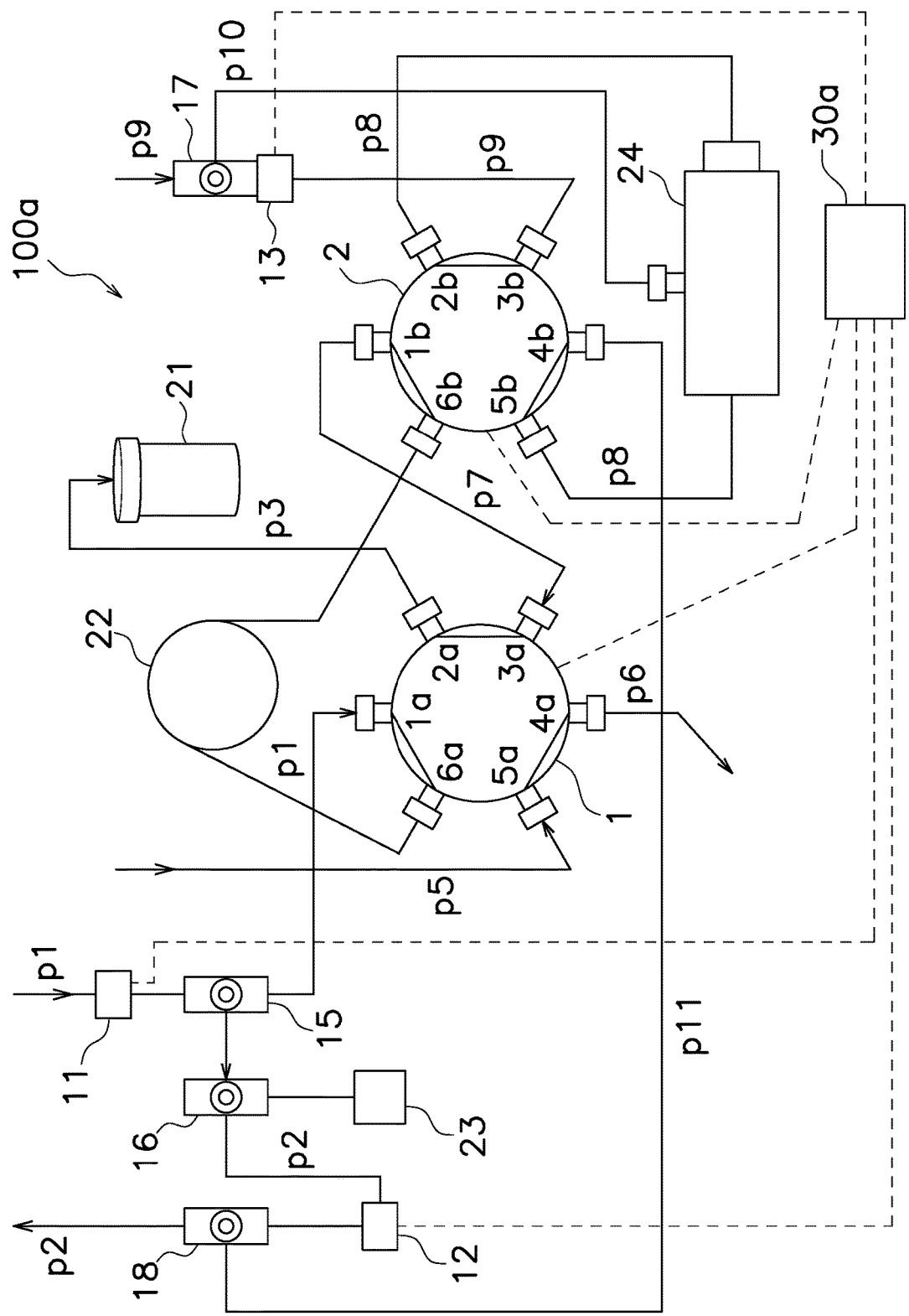
FIG. 7 is a diagram showing a configuration of a gas sample introduction device 100a (trap/loop dual-purpose device) of a second embodiment.

The gas sample introduction device 100a of this embodiment is a trap/loop dual-purpose device including both the sample loop 22 and the trap tube 24, as shown in FIG. 7. The gas sample introduction device 100a includes a sample container connection flow path p3, a pressurizing gas supply flow path p1, a gas discharge flow path p2, a sample loop 22, a trap tube 24, a dry purge gas supply flow path p9, a carrier gas supply flow path p5, an analysis device connection flow path p6, a first flow path switching valve 1, a second flow path switching valve 2, a first open/close valve 11, a second open/close valve 12, a third open/close valve 13, a pressure sensor 23, and a controller 30a. The gas sample introduction device 100a includes a device for heating the sample container 21 and a device for piercing the needle into the sample container 21. The gas sample introduction device 100a may include a device for transferring the sample container 21 on the sample tray 200 to a predetermined position of the gas sample introduction device 100a.

The sample container 21, the sample container connection flow path p3, the pressurizing gas, the pressurizing gas supply flow path p1, the gas discharge flow path p2, the pressure sensor 23, the carrier gas, the carrier gas supply flow path p5, the analysis device connection flow path p6, the first flow path switching valve 1 are the same as those in the first embodiment, and therefore the descriptions thereof will be omitted.

The second flow path switching valve 2 has six ports 1b to 6b. The second flow path switching valve 2 switches the connection status of ports between a first state and a second state. In the first state, as shown in FIG. 7, the second flow path switching valve 2 connects the port 6b and the port 1b, connects the port 2b and the port 3b, and connects the port 4b and the port 5b. The first state is also referred to as a loop state. In the second state, the second flow path switching valve 2 connects the port 1b and the port 2b, connects the port 3b and the port 4b, and connects the port 5b and the port 6b. The second state is also referred to as a trap state.

The sample loop 22 has a predetermined capacity and accommodates a sample gas. The sample loop 22 is connected to the port 6a of the first flow path switching valve 1 and the port 6b of the second flow path switching valve 2.

The trap tube 24 is provided with a cooler (not shown) and a heater (not shown). The cooler and the heater are controlled by the controller 30a. As the sample gas from the sample loop 22 passes through the trap tube 24, the certain components in the sample gas are adsorbed by the trap tube 24 when the trap tube 24 is cooled by the cooler. The capacity that the trap tube 24 absorbs the sample gas is several times or more of the capacity that the sample loop 22 accommodates the sample gas. Therefore, by making the trap tube 24 absorb the sample gas accommodated in the sample loop 22 a plurality of times, the trap tube 24 can adsorb the sample gas of an amount several times larger than the amount of the sample gas accommodated in the sample loop. The sample gas absorbed by the trap tube 24 is heated by the heater to be desorbed and is transferred to the analysis device by the carrier gas via the analysis device connection flow path p6.

By cooling the trap tube 24 with a cooler, water droplets adhere to the inside and the outside of the trap tube 24. The gas sample introduction device 100a of this embodiment supplies a dry purge gas to the inside and the outside of the trap tube 24 to remove water droplets or prevent water droplets from adhering. The dry purge gas is, for example, dry He. The dry purge gas supply flow path p9 is connected to the port 3b of the second flow path switching valve 2 via the branch pipe 17 and the third open/close valve 13 in the middle of the dry purge gas source. When the second flow path switching valve 2 has been switched to the first state, the port 3b is connected to the port 2b, and the flow path p8 connected to the port 2b is connected to the inside of the trap tube 24. The dry purge gas is supplied to the inside of the trap tube 24 via the flow paths p9 and p8. The dry purge gas passes through the dry purge gas supply flow path p9 and is branched by the branch pipe 17. Then, the dry purge gas is supplied to the outer side of the trap tube 24 via the flow path p10.

Note that formations indicating the open/close state of the first open/close valve 11, the second open/close valve 12, and the third open/close valve 13 and whether the first flow path switching valve 1 and the second flow path switching valve 2 are in the first state or the second state are referred to as valve formations. The valve formations mainly at the time of a leak check are shown in Table 2 as valve formations B1 to B6. When using the same valve formations when the sample is introduced, the valve formations B1 to B6 are used as appropriate.

TABLE 2

| Valve Formation | First opening and closing Valve 11 | Second opening and closing Valve 12 | Third open/close Valve 13 | First flow path switching valve 1 | Second flow path switching valve 2 |
|---|---|---|---|---|---|
| B1 | Open | Close | Close | First state (load) | Second state (trap) |
| B2 | Close | Close | Close | First state (load) | Second state (trap) |
| B3 | Open | Close | Close | Second state (inject) | First state (loop) |
| B4 | Close | Close | Close | Second state (inject) | First state (loop) |
| B5 | Open | Close | Close | First state (load) | First state (loop) |
| B6 | Close | Close | Close | First state (load) | First state (loops) |

The controller 30a is a computer. The controller 30a includes a processor and a memory. The controller 30a may further include a display and a user input, such as, e.g., a keyboard, a mouse, and a touch panel. Programs are stored in the memory. The programs are, for example, a sample introduction program, a leak check program, or the like. The processor executes the programs. The controller 30a controls the first open/close valve 11, the second open/close valve 12, the third open/close valve 13, the first flow path switching valve 1, the second flow path switching valve 2, and the sample heating device (not shown). The controller 30a may further control a device for transferring the sample from the sample tray to the gas sample introduction device 100, a device for piercing the needle into the sample container 21, a cooler of the trap tube 24, and a heater.

(5) Method of Introducing Gaseous Sample into Analysis Device 300 by Gas Sample Introduction Device 100a A method of introducing a gaseous sample into the analysis device 300 by the gas sample introduction device 100a will be described. Here, the method of introducing the sample gas into the analysis device 300 using both the trap tube 24 and the sample loop 22 will be described.

A liquid sample or a solid sample is placed in the sample container 21. The sample container 21 is placed at a predetermined position of the gas sample introduction device 100. Sample gases are caused to be generated in the headspace. The needle is pierced into the lid of the sample container 21. The above is the same as in the first embodiment, and therefore, the description thereof will be omitted.

In a state (i.e., in the status shown in the valve formation B5 in Table 2) in which the second open/close valve 12 and the third open/close valve 13 each are set to the closed state, the first flow path switching valve 1 is set to the first state (load state), and the second flow path switching valve 2 is set to the first state (loop status), the first open/close valve 11 is changed from the closed state to the open state. With this, the pressure of the pressurizing gas is applied to the headspace in the sample container 21 from the pressurizing gas supply flow path p1 via the sample loop 22, the flow path p7, and the sample container connection flow path p3. In other words, the headspace becomes the pressure of the pressurizing gas. Then, the first open/close valve 11 is changed from the open state to the closed state, and the second open/close valve 12 is changed from the closed state to the open state. Thereby, the sample gas in the headspace flows into the sample loop 22 together with the pressurizing gas. The pressure of the entire system becomes the pressure of the gas discharge flow path p2. The excessive pressurizing gas passes through the second open/close valve 12 and is discharged from the gas discharge flow path p2.

Next, the second flow path switching valve 2 is switched to the second state (trap state) with the first flow path switching valve 1 maintained in the first state (load state), the second open/close valve 12 is changed to the closed state, and the first open/close valve 11 is changed to the open state (valve formation B1). With this, the sample gas of the sample loop 22 is transferred to the trap tube 24. By cooling the trap tube 24 to a predetermined temperature, the predetermined components of the sample gas are adsorbed by the trap tube 24. The step of transferring the sample gas from the headspace of the sample container 21 to the sample loop 22 and the step of transferring the sample gas accommodated in the sample loop 22 to the trap tube 24 as described above are repeated. With this, it is possible to make the trap tube 24 absorb the sample gas of the multiple capacities of the sample loop.

In the above-described sample gas adsorption step of the trap tube 24, not only the sample component to be analyzed but also the moisture in the sample gas are collected to the inside of the trap tube 24. Therefore, the removal of such moisture (dry purge) is performed. The second flow path switching valve 2 is set to the first state (loop state, FIG. 11), and the third open/close valve 13 is set to the open state. By setting as described above, the dry purge gas is introduced to the inside of the trap tube 24 via the dry purge gas supply flow path p9, the ports 3b and 2b of the second flow path switching valve 2, and the flow path p8. The dry purge gas is discharged to the outside of the gas sample introduction device 100a via the flow path p8, the ports 5b and 4b of the second flow path switching valve 2, the flow path p11, the branch pipe 18, and the gas discharge flow path p2 together with the moisture inside the trap tube 24.

After the dry purge processing, the first flow path switching valve 1 is switched to the second state (inject state), and the second flow path switching valve 2 is switched to the second state (trap state). The trap tube 24 is heated to desorb the sample components adsorbed by the trap tube 24. The carrier gas is supplied to the carrier gas supply flow path p5. The carrier gas flows into the trap tube 24 from the carrier gas supply flow path p5 via the sample loop 22. Further, the carrier gas flows through the flow path p7 and the analysis device connection flow path p6 together with the desorbed sample gas in the trap tube 24 and is supplied to the analysis device 300.

(6) Leak Check Method of Gas Sample Introduction Device 100a

Figure 8A:
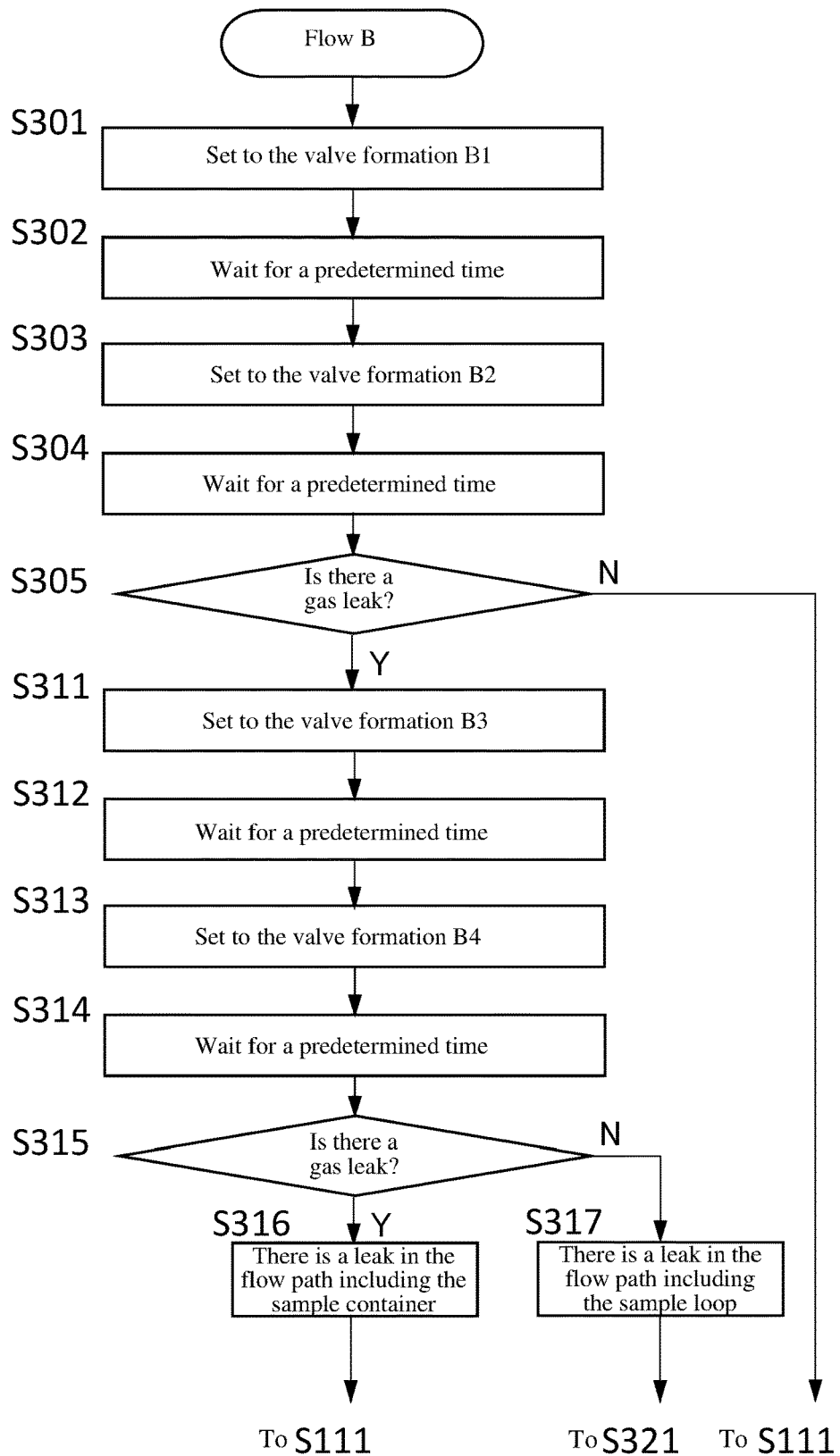
FIG. 8A is a flowchart showing a part of the leak check method of the gas sample introduction device 100a of the second embodiment.
Figure 8B:
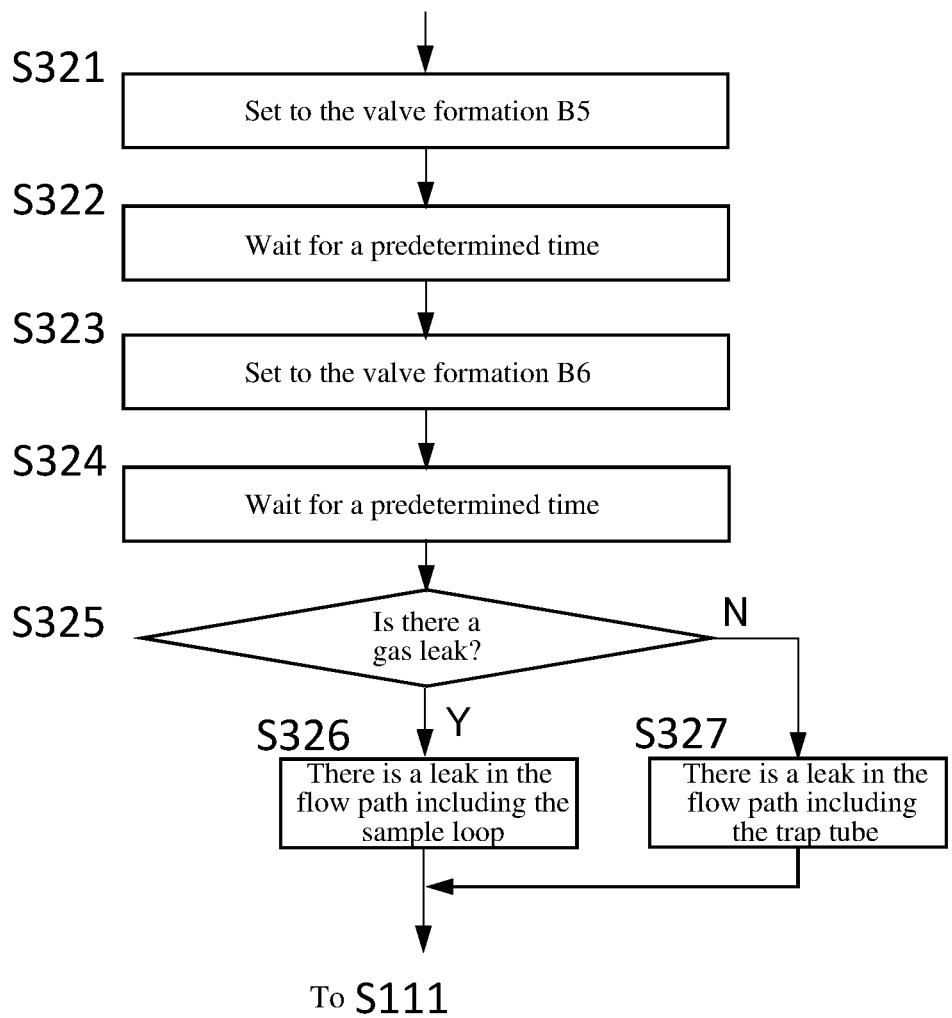
FIG. 8B is a flowchart showing a part of the leak check method of the gas sample introduction device 100a of the second embodiment.

The leak check method of the gas sample introduction device 100a according to the second embodiment will be described with reference to the drawings. FIG. 3, FIG. 8A, and FIG. 8B are flowcharts showing the leak check method.

Also in this embodiment, the steps up to Step S102 in FIG. 3 are the same as those in the first embodiment, and therefore the descriptions thereof will be omitted.

Next, in Step S103 of FIG. 3, the controller determines whether the gas sample introduction device is a loop dedicated device or a trap/loop dual-purpose device. In this embodiment, since the controller is a trap/loop dual-purpose device, the process proceeds to the flow B (FIG. 8A and FIG. 8B).

The flow B shown in FIG. 8A and FIG. 8B is the main processing of the leak checking. The flow B includes a first determination step (S301 to S305) for determining whether or not there is a gas leak in the main flow path of the gas sample introduction device 100 and a second determination step (S311 to S317) and a third determination step (S321 to S327) for identifying the location of the gas leak.

Figure 9:
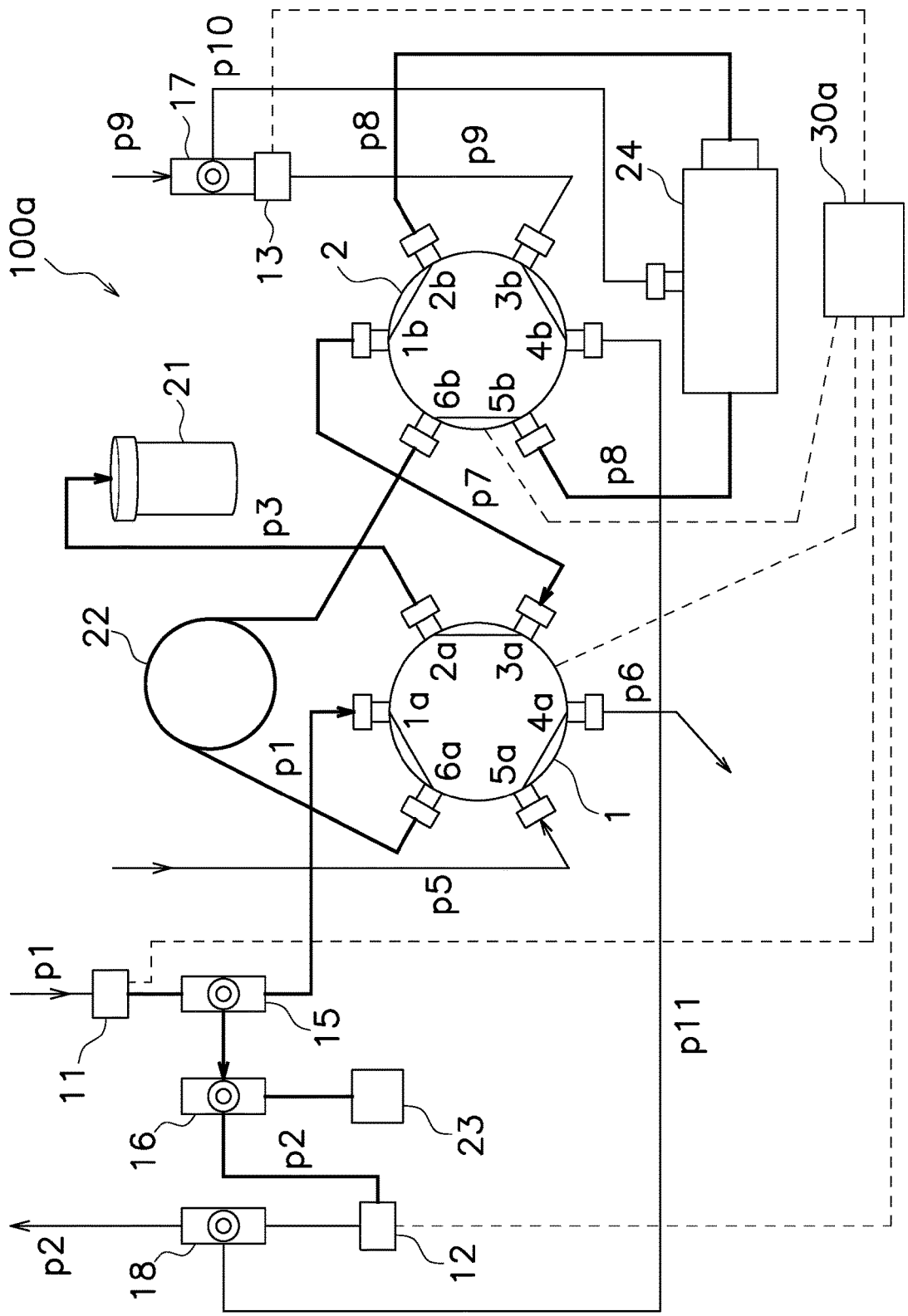
FIG. 9 is a diagram showing a thick line portion that becomes a high pressure in the second determination step during the leak check of the gas sample introduction device 100a of the second embodiment.

The first determination step is as follows:

First, in Step S301, the controller 30a sets the valve formation to a valve formation B1. More specifically, the controller 30a sets the second open/close valve 12 to the closed state, sets the third open/close valve 13 to the closed state, sets the first flow path switching valve 1 to the first state (load state), and sets the second flow path switching valve 2 to the second state (trap state). Then, in this state, the controller changes the first open/close valve 11 from the closed state to the open state. With this, the flow path of the gas sample introduction device 100 shown by the thick line in FIG. 9 is pressurized with the pressurizing gas. Then, the elapse of a preset predetermined time is waited (S302). The predetermined time means a time from when the pressurizing gas flows from the pressurizing gas supply flow path p1 into the entire flow path until when the pressure to be measured with the pressure sensor 23 is stabilized, when there is no gas leak. Further, in the flow B, since the second open/close valve 12 and the third open/close valve 13 are closed in any valve formation, the description in the subsequent Steps will be omitted.

Next, in Step S303, the controller 30a sets the valve formation to the valve formation B2. Specifically, the first open/close valve 11 is changed from the open state to the closed state without changing the states of other valves. As a result, the portion of the gas sample introduction device 100 indicated by the thick line in FIG. 9 is sealed in a state of being pressurized with the pressurizing gas. That is, the portions to be sealed are the portion of the pressurizing gas supply flow path p1 on the side of the first flow path switching valve 1 than the first open/close valve 11, the portion of the gas discharge flow path p2 between the second open/close valve 12 and the branch pipe 15, the ports 1a, 6a, 2*a*, and 3*a* of the first flow path switching valve 1, the sample loop 22, the flow path p7, the trap tube 24 and the trap tube connection flow path p8, the ports 1*b*, 2*b*, 5*b*, and 6*b* of the second flow path switching valve 2, the sample container connection flow path p3 and the inside of the sample container 21. Then, the elapse of a preset predetermined time is waited (S304). The predetermined time may be the same as or different from the predetermined time in Step S302.

Next, in Step S305, the controller 30*a* determines whether or not a gas leak has occurred. In other words, the controller 30*a* determines whether or not the measured value of the pressure sensor 23 is a normal (no gas leak) gas pressure. Normally, when the measured pressure is close to or sufficiently higher than the pressure of the pressurizing gas, it is determined to be normal (no gas leak). When it is considerably lower than the pressure of the pressurizing gas, it is determined that it is not normal (there is a gas leak). When it is determined that there is no gas leak, the process returns to FIG. 3 and proceeds to Step S111. When it is determined that there is a gas leak, the process proceeds to Step S311 of the second determination step.

Next, the second determination step will be described.

Figure 10:
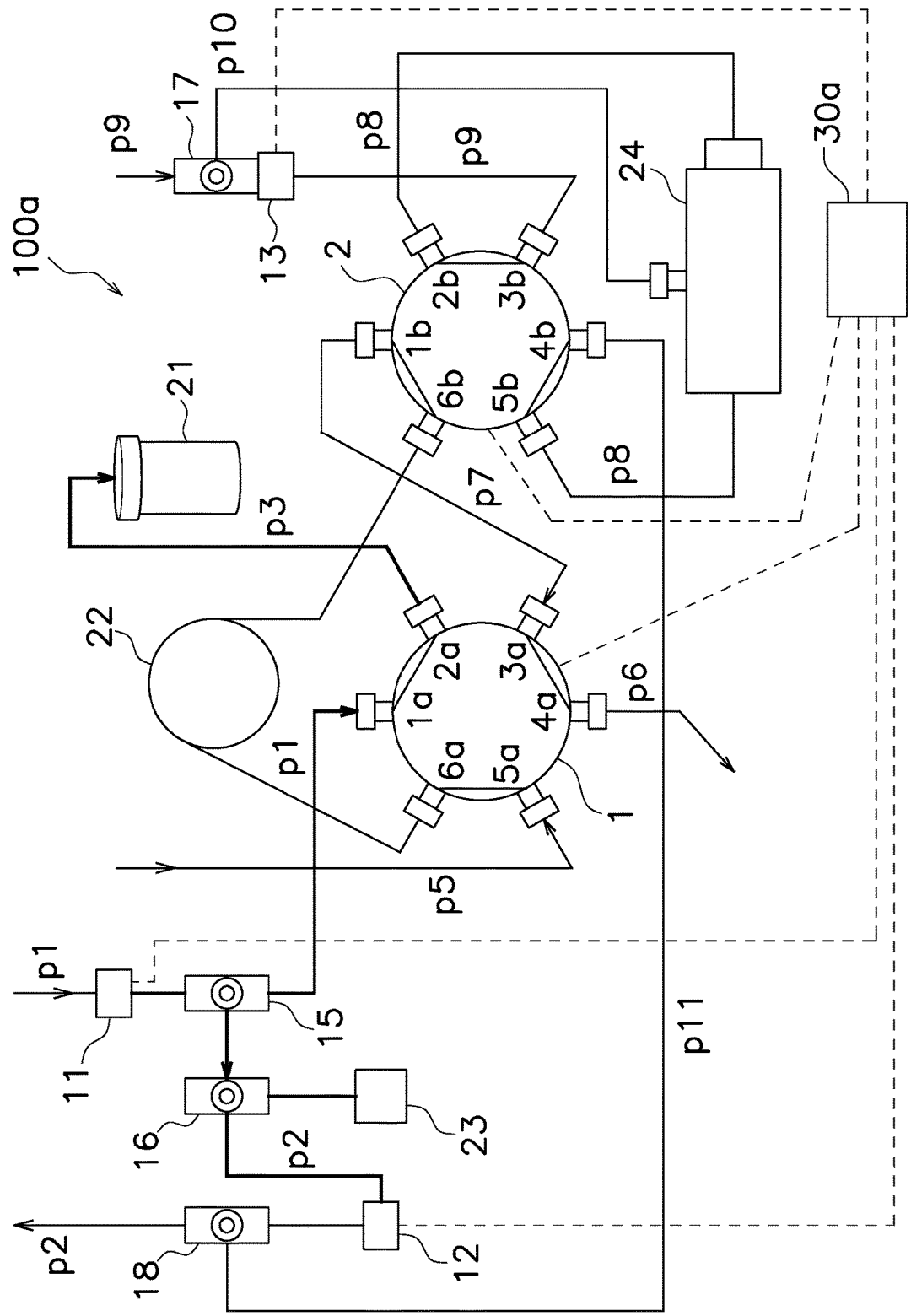
FIG. 10 is a diagram showing a thick line portion that becomes a high voltage in a second determination step in the leak check of gas sample introduction device 100a of a second embodiment.

In Step S311, the controller 30*a* sets the valve formation to the valve formation B3. More specifically, the controller 30*a* sets the first flow path switching valve 1 to the second state (inject state) and sets the second flow path switching valve 2 to the first state (looped). In this state, the controller 30*a* changes the first open/close valve 11 from the closed state to the open state. With this, the portion of the gas sample introduction device 100 indicated by the thick line in FIG. 10 is pressurized by the pressurizing gas. Then, the elapse of a preset predetermined time is waited (S312). The predetermined time means a time from when the pressurizing gas flows from the pressurizing gas supply flow path p1 until when the pressure to be measured by the pressure sensor 23 is stabilized, when there is no gas leak. The predetermined time in Step S312 may be the same as or different from the predetermined time in Step S302.

Next, in Step S313, the controller 30*a* sets the valve formation to the valve formation B4. Specifically, the controller 30*a* changes the first open/close valve 11 from the open state to the closed state without changing the states of other valves. With this, the portion of the gas sample introduction device 100*a* shown by the thick line in FIG. 10 is sealed in a state of being pressurized by the pressurizing gas. That is, the portions to be sealed are the portion of the pressurizing gas supply flow path p1 on the side of the first flow path switching valve 1 than the first open/close valve 11, the portion of the gas discharge flow path p2 between the second open/close valve 12 and the branch pipe 15, the ports 1*a* and 2*a* of the first flow path switching valve 1, the sample container connection flow path p3, and the inside of the sample container 21. Then, the elapse of a preset predetermined time is waited (S314). The predetermined time here may be the same as or different from the predetermined time of Step S312

Next, in Step S315, the controller 30*a* determines whether or not a gas leak has occurred. In other words, the controller 30*a* determines whether or not the measured value of the pressure sensor 23 is a normal (no gas leak) gas pressure. Normally, when the measured pressure is close to or sufficiently higher than the pressure of the pressurizing gas, it is determined that it is normal (no gas leak). When it is considerably lower than the pressure of the pressurizing gas, it is determined that it is not normal (there is a gas leak).

In Step S315, when it is determined that there is a gas leak, the controller 30*a* determines that there are gas leaks in the portion pressurized in the second determination step (S316) and the portion indicated by the thick line in FIG. 10 (S316). In other words, it is determined that there is a gas leak in the portion of the pressurizing gas supply flow path p1 on the side of the first flow path switching valve 1 than the first open/close valve 11, the portion of the gas discharge flow path p2 between the second open/close valve 12 and the branch pipe 15, the ports 1*a* and 2*a* of the first flow path switching valve 1, the sample container connection flow path p3, and the inside of the sample container 21. That is, it is determined that there is a gas leak in the flow path including the sample container connection flow path p3.

When it is determined in Step S315 that there is no gas leak, the process may proceed to the third determination step (S321) without via Step S317. The process may go through Step S317 before proceeding to the third determination step. In Step S317, the controller 30*a* determines that there is a gas leak in the flow path including the sample loop 22. In particular, the flow path including the sample loop 22 means a flow path including the ports 6*a* and 3*a* of the first flow path switching valve 1, the sample loop 22, the flow path p7, the trap tube 24 and the trap tube connecting flow path p8, the ports 1*b*, 2*b*, 5*b*, and 6*b* of the second flow path switching valve 2. When it is determined in Step S317 that there is a leak in a flow path including the sample loop 22, the leak check may be completed and the process may proceed to Step S111. Further, the process may proceed to the third determination step (S321) to identify the location of the leak. Here, the description will be continued on the assumption that the process proceeds to the third determination step (S321).

Figure 11:
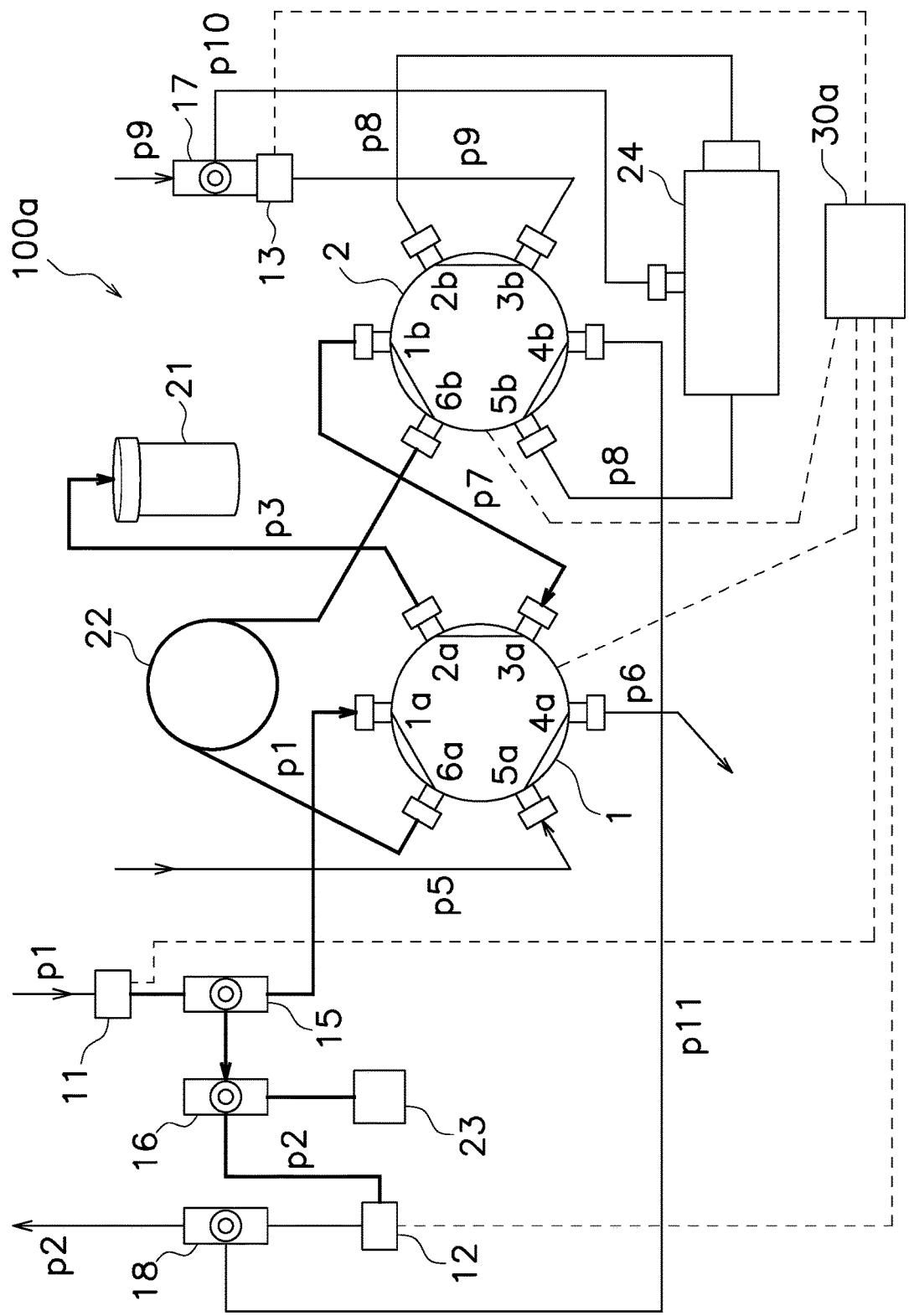
FIG. 11 is a diagram showing a thick line portion that becomes a high pressure in a third determination step during the leak check of the gas sample introduction device 100a of the second embodiment.

The third determination step is as follows:

In Step S321, the controller 30*a* sets the valve formation to the valve formation B5. More specifically, the controller 30*a* sets the first flow path switching valve 1 to the first state (load state) without changing the states of other valves and changes the first open/close valve 11 from the closed state to the open state. With this, the portion of the gas sample introduction device 100 indicated by the thick line in FIG. 11 is pressurized by the pressurizing gas. Then, the elapse of a preset predetermined time is waited (S322). The predetermined time means a time from when the pressurizing gas flows from the pressurizing gas supply flow path p1 until when the pressure measured by the pressure sensor 23 is stabilized, when there is no gas leak. The predetermined time in Step S322 may be the same as or different from the predetermined time in Step S302.

Next, in Step S323, the controller 30*a* sets the valve formation to the valve formation B6. Specifically, the controller 30*a* changes the first open/close valve 11 from the open state to the closed state without changing the states of other valves. With this, the flow path of the gas sample introduction device 100 shown by the thick line in FIG. 11 is sealed in a state of being pressurized by the pressurizing gas. That is, the portions to be sealed are the portion of the pressurizing gas supply flow path p1 on the side of the first flow path switching valve 1 than the first open/close valve 11, the portion of the gas discharge flow path p2 between the second open/close valve 12 and the branch pipe 15, the ports 6*a*, 1*a*, 2*a*, and 3*a* of the first flow path switching valve 1, the sample loop 22, the flow path p7, the ports 6*b* and 1*b* of the second flow path switching valve 2, the sample container connection flow path p3, and the inside of the sample container 21. Then, the elapse of a preset predetermined time is waited (S324). The predetermined time may be the same as or different from the predetermined time in Step S322.

Next, in Step S325, the controller 30a determines whether or not a gas leak has occurred. In other words, the controller 30a determines whether or not the measured value of the pressure sensor 23 is a normal (no gas leak) gas pressure. Normally, when the measured pressure is close to or sufficiently higher than the pressure of the pressurizing gas, it is determined that it is normal (no gas leak). When it is considerably lower than the pressure of the pressurizing gas, it is determined that it is not normal (there is a gas leak).

When the controller 30a determines that there is a gas leak in Step S325, it is pressurized in the third determination step. But it is determined that there is a gas leak in the portion to which no pressure has been applied in the second determination step (S326). That is, it is determined that there is a gas leak in the sample loop 22, the flow path p7, the ports 6a and 3a of the first flow path switching valve 1, or the port 6b, 1b of the second flow path switching valve 2. In other words, it is determined that there is a gas leak in the flow path including the sample loop 22.

When the controller 30a has determined that there is no gas leak in Step S325, it is pressurized in the first determination step. But, it is determined that there is a gas leak in the portion to which it was not pressurized in the third determination step (S327). That is, it is determined that there is a leak in the connecting flow path p8 between the trap tube 24 and the trap tube, or the port 2b, 5b of the second flow path switching valve 2. In other words, it is determined that there is a gas leak in the flow path including the trap tube 24.

Next, returning to FIG. 3, the controller 30a pulls the needle out of the sample container 21 (S111), transfers the sample container 21 to the sample tray 200 (S112), and ends the process.

In the gas sample introduction device 100a and the sample container 21 of this embodiment, it is considered that a gas leak occurs especially in the sample container 21 which is covered by the user, the port 6a of the first flow path switching valve 1 to which the sample loop 22 is connected, and the port 6b of the second flow path switching valve 2. According to the leak check method of the present disclosure, it is possible to specify the flow path including which of the above in which a gas leak has occurred by the gas leak determination of Step S315 and S325.

Furthermore, by executing the above-described third determination step (Steps S321 to S327), it is possible to identify whether there is a gas leak in the flow path including the sample loop or whether there is a gas leak in the flow path including the trap tube.

In the leak check method (program) of this embodiment, in Step S103, it is determined whether it is a loop dedicated device or a trap/loop dual-purpose device. In a case where it is a method (program) to be used exclusively for a trap/loop dual-purpose device, the process may proceed to the flow B by omitting Step S103.

Further, in the leak check method of this embodiment, in any of the first determination step, the second determination step, and the third determination step, it is determined whether or not there is a gas leak by checking the degree of decrease in the gas pressure after introducing the pressurizing gas and then sealing the pressurized gas flow path. In either one of or all of the determination steps, it may be determined whether or not there is a gas leak by changing the first open/close valve from the closed state to the open state and checking the degree of the pressure increase of the gas flow path in the process of introducing the pressurizing gas.

The gas sample introduction device 100a of this embodiment has the flow path configuration shown in FIG. 7, but the present disclosure is not limited thereto. For example, although the gas sample introduction device 100a uses the first flow path switching valve 1 and the second flow path switching valve 2, each having six ports, the number of flow path switching valves and the number of the ports may be different from the above. The valve formation is not necessarily required to be the same as in this embodiment. As long as it is possible to switch the flow paths capable of being pressurized, some sort of the gas leak location can be identified by the valve formation switch.

Although some embodiments of the present disclosure have been described above, the present disclosure is not limited to the above-described embodiments, and various modifications can be made without departing from the gist of the present disclosure. In particular, the plurality of embodiments described herein may be arbitrarily combined as needed.

(7) Aspects

It will be understood by those skilled in the art that the plurality of exemplary embodiments described above is illustrative of the following aspects.

(Item 1)

A gas sample introduction device according to one aspect of the present disclosure is a gas sample introduction device for introducing a sample gas into an analysis device, comprising:

a sample container connection flow path connected to a space in a sample container;

a pressurizing gas supply flow path configured to supply a pressurizing gas for pressurizing an inside of the sample container;

a gas discharge flow path configured to discharge the pressurizing gas;

a sample loop configured to store the sample gas from the sample container;

a first flow path switching valve configured to switch between a first state in which the sample loop is connected between the pressurizing gas supply flow path and the sample container connection flow path and a second state in which the pressurizing gas supply flow path and the sample container connection flow path are connected without via the sample loop;

a first open/close valve arranged in a middle of the pressurizing gas supply flow path;

a second open/close valve arranged in a middle of the gas discharge flow path;

a pressure sensor configured to measure a pressure between the first open/close valve of the pressurizing gas supply flow path and the first flow path switching valve or between the second open/close valve of the gas discharge flow path and the first flow path switching valve; and a controller configured to control the first open/close valve, the second open/close valve, and the first flow path switching valve, wherein the controller switches the first open/close valve from an open state to a closed state in a state in which the first flow path switching valve is in the first state and the second open/close valve is in a closed state and then performs a first determination of whether or not there is a gas leak based on a measured value of the pressure sensor, and wherein when the controller has determined that there is the gas leak, the controller switches the first open/close valve from the open state to the closed state in a state in which the first flow path switching valve is in a second state and the second open/close valve is in a closed state and then identifies a location of the gas leak by performing a second determination of whether or not there is a gas leak based on a measured value of the pressure sensor.

The gas sample introduction device as recited in the above-described Item 1 can identify the location of the gas leak in either case of the loop dedicated device and the trap/loop dual-purpose device by performing the gas leak determination processing twice.

(Item 2)

In the gas sample introduction device as recited in the above-described Item 1, prior to the first determination and/or the second determination, the controller waits for a predetermined time to elapse with the first open/close value opened and subsequently waits for a predetermined time to elapse with the first open/close valve closed, and then performs the first determination and/or the second determination.

The gas sample introduction device as recited in the above-described Item 2 performs the determination of whether or not there is a gas leak by waiting for the elapse of a predetermined time after the valve switching, which enables a more accurate determination of whether or not there is a gas leak.

(Item 3)

In the gas sample introduction device as recited in the above-described Item 1, when the controller determines that there is a gas leak in the second determination, the controller determines that there is a gas leak in a flow path including the sample container connection flow path and the sample container, and when the controller determines that there is no gas leak in the second determination, the controller determines that there is a gas leak in a flow path including the sample loop or a port of the first flow path switching valve connecting the sample loop.

The gas sample introduction device as recited in the above-described Item 3 can specify which of the sample container connection flow path in which a gas leak is likely to occur or the flow path including the first flow path switching valve has occurred the gas leak.

(Item 4)

The gas sample introduction device as recited in any one of the above-described Items 1 to 3, further comprises:

a trap tube configured to adsorb a predetermined component in the sample gas; and a second flow path switching valve capable of switching between a first state in which the trap tube is not connected to the sample loop and a second state in which the trap tube is connected to the sample loop, wherein the controller performs the first determination in a state in which the second flow path switching valve is in the second state and then further performs the second determination in a state in which the second flow path switching valve has been switched to the first state, wherein when the controller has determined that there is a gas leak in the second determination, the controller switches the first open/close value from the open state to the closed state in a state in which the first flow path switching valve has been switched from the second state to the first state and performs a third determination of whether or not there is a gas leak, based on a measured value of the pressure sensor to further identify a location of the gas leak.

The gas sample introduction device as recited in the above-described Item 4 can identify the location of the gas leak more detail in the case of a trap/loop dual-purpose device.

(Item 5)

In the gas sample introduction device as recited in the above-described Item 4, prior to the third determination, the controller waits for a predetermined time to elapse with the first open/close valve closed, subsequently waits for a predetermined time to elapse with the first open/close valve closed, and then performs the third determination.

The gas sample introduction device as recited in the above-described Item 5 determines whether or not there is a gas leak by waiting for a predetermined time to elapse after changing the valve state before the third determination. Therefore, it is possible to more accurately determine the location of the gas leak in the case of a trap/loop dual-purpose device.

(Item 6)

In the gas sample introduction device as recited in the above-described Item 4 or 5, when the controller determines that there is a gas leak in the third determination, the controller determines that there is a gas leak in a flow path including the sample loop or in a port of the first flow path switching valve or the second flow path switching valve connecting the sample loop, and when the controller determines that there is no gas leak in the third determination, the controller determines that there is a gas leak in a flow path including the trap tube.

The gas sample introduction device as recited in the above-described Item 6 can specify, in the case of a trap/loop dual-purpose device, whether or not there is a gas leak in the flow path including the sample loop or whether or not there is a gas leak in the flow path including the trap tube, by the third determination.

(Item 7)

In a leak check method of a gas sample introduction device according to one aspect of the present disclosure, the gas sample introduction device comprises:

a sample container connection flow path configured to be connected to a space in a sample container;

a pressurizing gas supply flow path configured to supply a pressurizing gas for pressurizing an inside of the sample container;

a gas discharge flow path configured to discharge the pressurizing gas;

a sample loop configured to store the sample gas from the sample container;

a first flow path switching valve configured to switch between a first state in which the sample loop is connected between the pressurizing gas supply flow path and the sample container connection flow path and a second state in which the pressurizing gas supply flow path and the sample container connection flow path are connected without via the sample loop;

a first open/close valve arranged in a middle of the pressurizing gas supply flow path;

a second open/close valve arranged in a middle of the gas discharge flow path;

a pressure sensor configured to measure a pressure between the first open/close valve of the pressurizing gas supply flow path and the first flow path switching valve or between the second open/close valve of the gas discharge flow path and the first flow path switching valve; and a controller configured to control the first open/close valve, the second open/close valve, and the first flow path switching valve, and the leak check method comprises:

a first determination step of performing a determination of whether or not there is a gas leak such that the controller switches the first open/close valve from an open state to a closed state in a state in which the first flow path switching valve is in the first state and the second open/close valve is in a closed state and then performs a determination of whether or not there is a gas leak, based on a measured value of the pressure sensor; and a second determination step of identifying a location of the gas leak such that the controller switches the first open/close valve from an open state to a closed state in a state in which the first flow path switching valve is in a second state and the second open/close valve is in a closed state and then performs a second determination of whether or not there is a gas leak, based on a measured value of the pressure sensor.

The gas sample introduction device's leak check method as recited in the above-described Item 7 can identify the location of the gas leak of the gas sample introduction device by performing the gas leak determination processing twice in either case of where the sample introduction device is a loop dedicated device or where the sample introduction device is a trap/loop dual-purpose device.

(Item 8)

In the leak check method of a gas sample introduction device as recited in the above-described Item 7, the gas sample introduction device further comprises:

a trap tube configured to adsorb a predetermined component in the sample gas; and a second flow path switching valve capable of switching between a first state in which the trap tube is not connected to the sample loop and a second state in which the trap tube is connected to the sample loop, in the leak check method, the controller controls the second flow path switching valve so as to be switched to a second state in the first determination step and further controls the second flow path switching valve so as to be switched to a first state in the second determination step, and the leak check method further comprises a third determination of further identifying a location of a gas leak such that when the controller has determined that there is no gas leak in the second determination, the controller switches the first open/close valve from an open state to a closed state in a state in which the first flow path switching valve has been switched from the second state to the first state and performs a determination of whether or not there is a gas leak, based on a measured value of the pressure sensor.

The leak check method of the gas sample introduction device as recited in the above-described Item 8 can specify the location of the gas leak in a case where the gas sample introduction device is a trap/loop dual-purpose device.

The invention claimed is:

1. A gas sample introduction device for introducing a sample gas into an analysis device, comprising:

a sample container connection flow path connected to a space in a sample container;

a pressurizing gas supply flow path configured to supply a pressurizing gas for pressurizing an inside of the sample container;

a gas discharge flow path configured to discharge the pressurizing gas;

a sample loop configured to store the sample gas from the sample container;

a first flow path switching valve configured to switch between a first state in which the sample loop is connected between the pressurizing gas supply flow path and the sample container connection flow path and a second state in which the pressurizing gas supply flow path and the sample container connection flow path are connected without via the sample loop;

a first open/close valve, separate from the first flow path switching valve, arranged within the pressurizing gas supply flow path;

a second open/close valve, separate from the first flow path switching valve, arranged within the gas discharge flow path;

a pressure sensor configured to measure a pressure between the first open/close valve of the pressurizing gas supply flow path and the sample container connection flow path when the first flow path switching valve is in the first state and between the second open/close valve of the gas discharge flow path and the first flow path switching valve when the first flow path switching valve is in the second state; and a controller configured to control the first open/close valve, the second open/close valve, and the first flow path switching valve, wherein the controller switches the first open/close valve from an open state to a closed state in a state in which the first flow path switching valve is in the first state and the second open/close valve is in a closed state and then performs a first determination of whether or not there is a gas leak, based on a measured value of the pressure sensor, and wherein when the controller has determined that there is the gas leak, the controller switches the first open/close valve from the open state to the closed state in a state in which the first flow path switching valve is in a second state and the second open/close valve is in a closed state and then identifies a location of the gas leak by performing a second determination of whether or not there is a gas leak, based on a measured value of the pressure sensor.

2. The gas sample introduction device as recited in claim 1, wherein prior to the first determination and/or the second determination, the controller waits for a predetermined time to elapse with the first open/close value opened and subsequently waits for a predetermined time to elapse with the first open/close valve closed, and then performs the first determination and/or the second determination.

3. The gas sample introduction device as recited in claim 1, wherein when the controller determines that there is a gas leak in the second determination, the controller determines that there is a gas leak in a flow path including the sample container connection flow path and the sample container, and wherein when the controller determines that there is no gas leak in the second determination, the controller determines that there is a gas leak in a flow path including the sample loop or a port of the first flow path switching valve connecting the sample loop.

4. The gas sample introduction device as recited in claim 1, further comprising:

a trap tube configured to adsorb a predetermined component in the sample gas; and a second flow path switching valve capable of switching between a first state in which the trap tube is not connected to the sample loop and a second state in which the trap tube is connected to the sample loop, wherein the controller performs the first determination in a state in which the second flow path switching valve is in the second state and then further performs the second determination in a state in which the second flow path switching valve has been switched to the first state, and wherein when the controller has determined that there is a gas leak in the second determination, the controller switches the first open/close value from the open state to the closed state in a state in which the first flow path switching valve has been switched from the second state to the first state and performs a third determination of whether or not there is a gas leak, based on a measured value of the pressure sensor to further identify a location of the gas leak.

5. The gas sample introduction device as recited in claim 4, wherein prior to the third determination, the controller waits for a predetermined time to elapse with the first open/close valve closed, subsequently waits for a predetermined time to elapse with the first open/close valve closed, and then performs the third determination.

6. The gas sample introduction device as recited in claim 4, wherein when the controller determines that there is a gas leak in the third determination, the controller determines that there is a gas leak in a flow path including the sample loop or in a port of the first flow path switching valve or the second flow path switching valve connecting the sample loop, and wherein when the controller determines that there is no gas leak in the third determination, the controller determines that there is a gas leak in a flow path including the trap tube.

7. A leak check method of a gas sample introduction device for introducing a sample gas into an analysis device, wherein the gas sample introduction device comprises:

a sample container connection flow path configured to be connected to a space in a sample container;

a pressurizing gas supply flow path configured to supply a pressurizing gas for pressurizing an inside of the sample container;

a gas discharge flow path configured to discharge the pressurizing gas;

a sample loop configured to store the sample gas from the sample container;

a first flow path switching valve configured to switch between a first state in which the sample loop is connected between the pressurizing gas supply flow path and the sample container connection flow path and a second state in which the pressurizing gas supply flow path and the sample container connection flow path are connected without via the sample loop;

a first open/close valve, separate from the first flow path switching valve, arranged within the pressurizing gas supply flow path;

a second open/close valve, separate from the first flow path switching valve, arranged within the gas discharge flow path;

a pressure sensor configured to measure a pressure between the first open/close valve of the pressurizing gas supply flow path and the sample container connection flow path when the first flow path switching valve is in the first state and between the second open/close valve of the gas discharge flow path and the first flow path switching valve when the first flow path switching valve is in the second state; and a controller configured to control the first open/close valve, the second open/close valve, and the first flow path switching valve, and wherein the leak check method comprises:

a first determination step of performing a determination of whether or not there is a gas leak such that the controller switches the first open/close valve from an open state to a closed state in a state in which the first flow path switching valve is in the first state and the second open/close valve is in a closed state and then performs a determination of whether or not there is a gas leak, based on a measured value of the pressure sensor; and a second determination step of identifying a location of the gas leak such that the controller switches the first open/close valve from an open state to a closed state in a state in which the first flow path switching valve is in a second state and the second open/close valve is in a closed state and then performs a second determination of whether or not there is a gas leak, based on a measured value of the pressure sensor.

8. The leak check method of a gas sample introduction device as recited in claim 7, wherein the gas sample introduction device further comprises:

a trap tube configured to adsorb a predetermined component in the sample gas; and a second flow path switching valve capable of switching between a first state in which the trap tube is not connected to the sample loop and a second state in which the trap tube is connected to the sample loop, wherein in the leak check method, the controller controls the second flow path switching valve so as to be switched to a second state in the first determination step and further controls the second flow path switching valve so as to be switched to a first state in the second determination step, and wherein the leak check method further comprises a third determination of further identifying a location of a gas leak such that when the controller has determined that there is no gas leak in the second determination, the controller switches the first open/close valve from an open state to a closed state in a state in which the first flow path switching valve has been switched from the second state to the first state and performs a determination of whether or not there is a gas leak, based on a measured value of the pressure sensor.

* * * * *